US 8,104,326 B2

(12) United States Patent
Tipler et al.

(10) Patent No.: US 8,104,326 B2
(45) Date of Patent: Jan. 31, 2012

(54) METHODS AND DEVICES FOR CIRCULATING AIR

(75) Inventors: Andrew Tipler, Trumbull, CT (US);
James Botelho, Danbury, CT (US);
Avinash Dalmia, Hamden, CT (US);
Michael J. Rafa, Weston, CT (US);
John Vanderhoef, Stratford, CT (US);
Paul Schallis, Ridgefield, CT (US); Neal Green, Southbury, CT (US); David J. Scott, Wallingford, CT (US); John McCaffrey, Avon, CT (US); Paul St. Cyr, Warren, MA (US); E. Joel McCorkle, Woodbury, CT (US);
Guiseppe Coppola, Shelton, CT (US)

(73) Assignee: PerkinElmer LAS, Inc., Waltham, MA (US)

( * ) Notice: Subject to any disclaimer, the term of this patent is extended or adjusted under 35 U.S.C. 154(b) by 559 days.

(21) Appl. No.: 11/841,054

(22) Filed: Aug. 20, 2007

(65) Prior Publication Data

US 2008/0105033 A1 May 8, 2008

Related U.S. Application Data

(60) Provisional application No. 60/822,851, filed on Aug. 18, 2006, provisional application No. 60/823,533, filed on Aug. 25, 2006.

(51) Int. Cl.
*G01N 30/04* (2006.01)
(52) U.S. Cl. .......... 73/23.42; 73/23.36; 96/102
(58) Field of Classification Search ........... 73/23.35, 73/23.36, 23.42; 96/101, 102
See application file for complete search history.

(56) References Cited

U.S. PATENT DOCUMENTS

| 3,438,243 | A | | 4/1969 | Parks, Jr. et al. |
| 3,958,552 | A | * | 5/1976 | Lawler ................. 126/247 |
| 4,181,613 | A | * | 1/1980 | Welsh et al. ............ 210/179 |
| 4,544,024 | A | * | 10/1985 | Baggott ................ 165/48.1 |
| 4,752,216 | A | * | 6/1988 | Hurrell ................. 432/48 |
| 6,248,158 | B1 | | 6/2001 | Abdel-Rahman et al. |
| 6,494,939 | B1 | | 12/2002 | Tipler |
| 6,814,785 | B2 | | 11/2004 | Tipler et al. |
| 6,824,656 | B2 | | 11/2004 | Dalmia et al. |
| 6,872,290 | B2 | | 3/2005 | Dalmia et al. |
| 6,908,538 | B2 | | 6/2005 | Dalmia et al. |
| 6,932,941 | B2 | | 8/2005 | Prohaska et al. |
| 7,013,707 | B2 | | 3/2006 | Prohaska et al. |
| 7,237,430 | B2 | | 7/2007 | Prohaska et al. |
| 7,311,757 | B2 | | 12/2007 | Tipler et al. |
| 7,411,160 | B2 | * | 8/2008 | Duncan et al. ............ 219/400 |
| 2005/0258088 | A1 | * | 11/2005 | Botelho et al. ........... 210/198.2 |
| 2006/0008385 | A1 | | 1/2006 | Millor, II |
| 2006/0075802 | A1 | | 4/2006 | Prohaska et al. |
| 2006/0278076 | A1 | | 12/2006 | Tipler |

FOREIGN PATENT DOCUMENTS

| JP | 2003-344376 | 12/2003 |
| JP | 2004-212357 | 7/2004 |
| WO | 2005108975 | 5/2005 |

* cited by examiner

*Primary Examiner* — Daniel Larkin
(74) *Attorney, Agent, or Firm* — Lando & Anastasi, LLP

(57) ABSTRACT

A gas chromatography system comprising a sample introduction device, an oven coupled to the sample introduction device and a detector coupled to the oven is disclosed. In certain examples, the oven may be configured to receive a chromatography column in a space in the oven. In some examples, the oven may be constructed and arranged to provide a substantially constant temperature to the space during an analysis stage of the gas chromatography system.

19 Claims, 33 Drawing Sheets

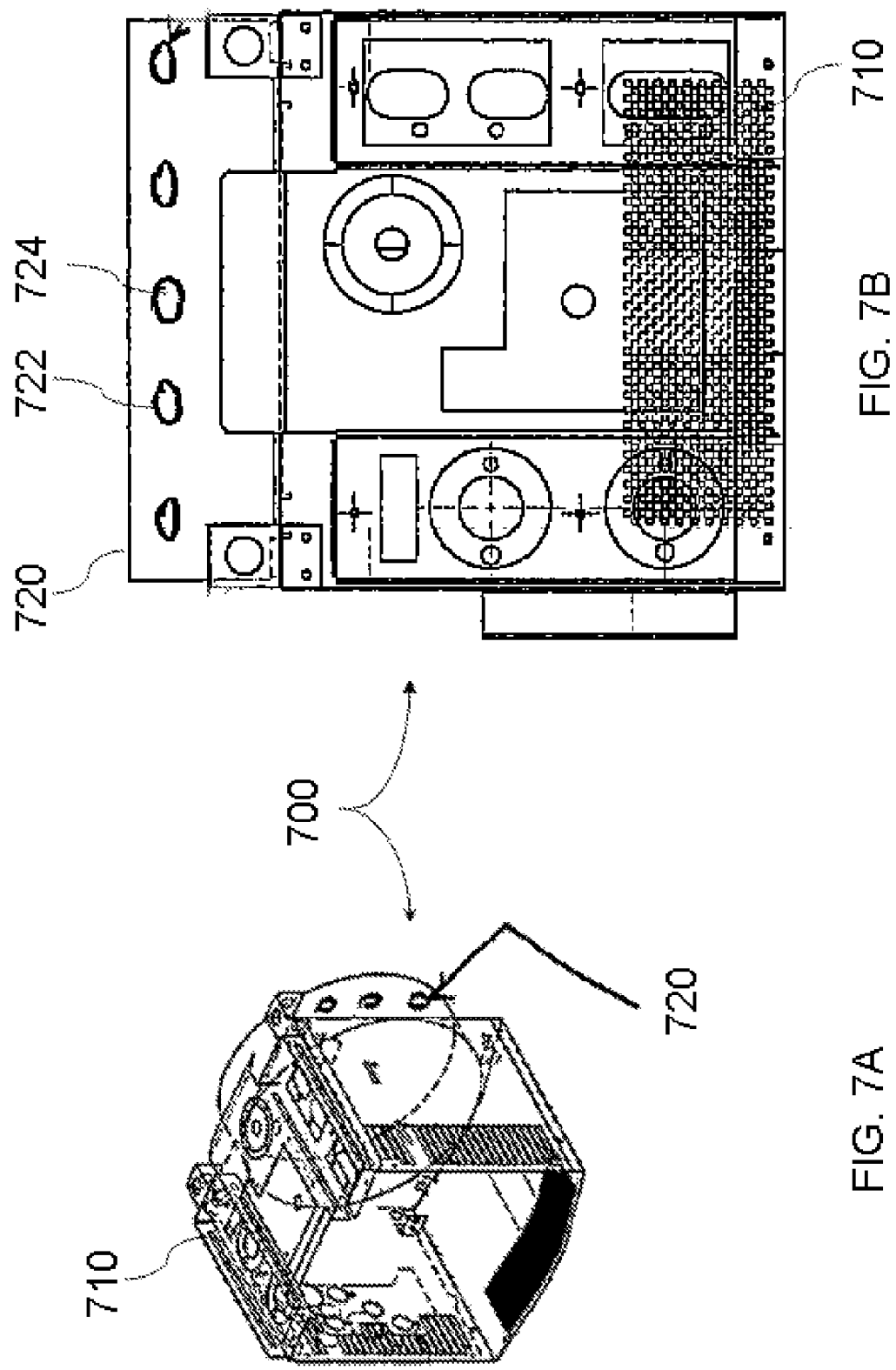

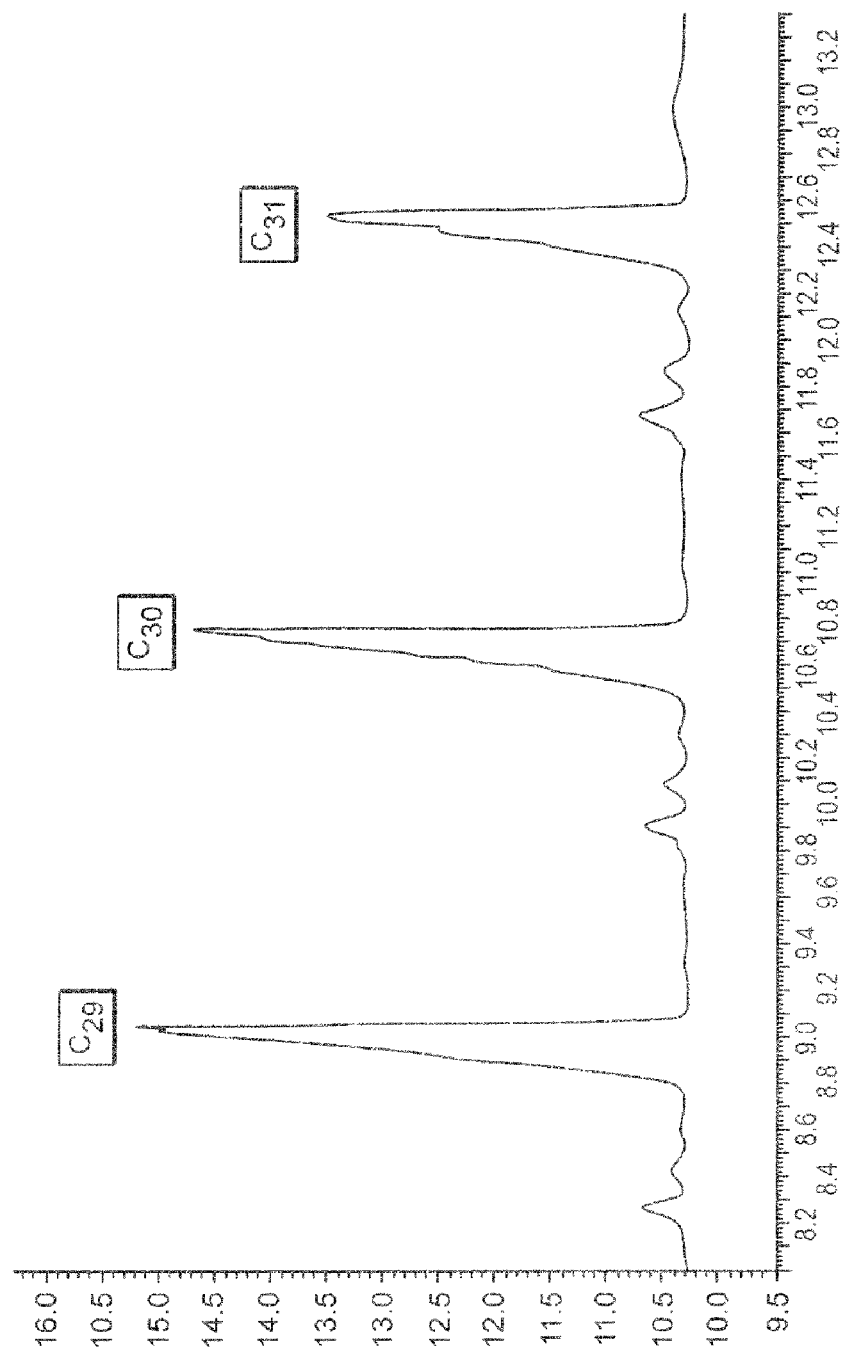

METHODS AND DEVICES FOR CIRCULATING AIR

PRIORITY APPLICATIONS

This application claims priority to U.S. Provisional Application No. 60/822,851 filed on Aug. 18, 2006 and to U.S. Provisional Application No. 60/823,533 filed on Aug. 25, 2006, the entire disclosure of each of which is hereby incorporated herein by reference for all purposes.

TECHNOLOGICAL FIELD

Examples disclosed herein relate generally to methods and systems for circulating air. More particularly, certain examples disclosed herein relate generally to methods and systems for circulating air in an oven of a chromatography system.

BACKGROUND

Gas chromatography (GC) ovens need to operate efficiently in two modes—heating (during analysis) and cooling (after analysis is complete to prepare for the next analysis). A double walled oven liner and shrouded fan move air very effectively during cooling (inlet and vent open) but not so effectively during heating (inlet and vent closed).

SUMMARY

In accordance with a first aspect, a gas chromatography system comprising a sample introduction device, an oven coupled to the sample introduction device and a detector coupled to the oven is provided. In certain examples, the oven may be configured to receive a chromatography column in a space in the oven. In other examples, the oven may be constructed and arranged to provide a substantially constant temperature to the space during an analysis stage of the gas chromatography system.

In certain examples, the oven may comprise a recirculation path configured to circulate air to provide the substantially constant temperature to the space during the analysis stage. In other examples, the recirculation path may include a shroud with at least one through-hole. In some examples, the recirculation path may include a shroud comprising at least one air scoop. In additional examples, the oven may further comprise an air intake aperture and an air exhaust aperture, wherein the position of at least one of the air intake aperture and the air exhaust aperture may be adjusted during the analysis stage of the gas chromatography system. In certain examples, the oven may further comprise a fan that may be modulated to rotate at two or more speeds during operation of the oven. In some examples, the fan may be fluidically coupled to at least one of the air intake aperture and the air exhaust aperture. In other examples, the gas chromatography system may further comprise a vent fluidically coupled to the air exhaust aperture and configured to exhaust hot air away from the space in oven. In certain examples, the detector of the system may be selected from the group consisting of an ionization detector, a hot wire detector, a thermal conductivity detector, a nitrogen phosphorous detector, a photometric detector, and a mass spectrometer. In some examples, the oven may be configured to provide a substantially constant injection-to-injection time that is provided by circulation of air by the recirculation path.

In accordance with another aspect, a gas chromatography system comprising an oven constructed and arranged with a fan that may be modulated to rotate at two or more speeds during operation of the oven is provided. In some examples, the fan may be modulated to rotate at a first speed of about 1400 rpm during an analysis stage and may be modulated to rotate at a second speed of about 2800 rpm during a cool down stage. In certain examples, the gas chromatography system may further comprise a programmable DC motor coupled to the fan. In some examples, the gas chromatography system may further comprise a controller coupled to the motor and configured to alter the fan speed during a cool down stage of the gas chromatography system.

In accordance with an additional aspect, a gas chromatography system comprising a sample introduction device, an oven, a detector and a fluid flow path configured to fluidically couple the sample introduction device, the oven and the detector is disclosed. In some examples, the oven comprises an air intake aperture and an air exhaust aperture, and a position of at least one of the air intake aperture and the air exhaust aperture may be adjusted during an analysis stage of the gas chromatography system. In certain examples, the gas chromatography system may further comprise a fan fluidically coupled to at least one of the air intake aperture and the air exhaust aperture. In other examples, the gas chromatography system may further comprise a programmable motor coupled to the fan and configured to modulate a fan speed of the fan. In some examples, the gas chromatography system may further comprise a recirculation path in the oven, and the recirculation path may be configured to circulate air to provide a substantially constant temperature to a space in the oven during the analysis stage. In certain examples, the recirculation path may include a shroud with at least one through-hole or a shroud comprising at least one air scoop.

In accordance with another aspect, a chromatography system comprising an oven constructed and arranged with an air intake aperture, an air exhaust aperture, a recirculation path configured to provide circulation of air in the oven during an analysis stage, and a fan that may be modulated to rotate at two or more speeds during operation of the oven is disclosed. In some examples, the recirculation path may include a shroud with at least one through-hole or a shroud comprising at least one air scoop. In other examples, the chromatography system may further comprise a programmable motor coupled to the fan.

In accordance with an additional aspect, a method of configuring a gas chromatography system to provide a substantially constant temperature in a space of the gas chromatography system configured to receive a chromatography column is provided. In certain examples, the method comprises configuring an oven with a recirculation path that comprises a shroud with at least one through-hole, a shroud with at least one air scoop, or both. In some examples, the method may further comprise configuring the gas chromatography system with a fan that is constructed and arranged to be modulated to rotate at two or more speeds during operation of the oven.

In accordance with another aspect, a method of performing an analysis using a gas chromatography system is disclosed. In certain examples, the method comprises introducing a sample into the gas chromatography system comprising an oven configured with a fan that is constructed and arranged to be modulated to rotate at two or more speeds during operation of the oven, separating species in the sample using a temperature ramp, wherein during the temperature ramp the fan is modulated at a first speed, and cooling the oven by modulating the fan at a second speed. In some examples, the method may further comprise opening an air inlet aperture and an air exhaust aperture during the cooling step. In other examples, the method may further comprise configuring the oven with a recirculation path that comprises a shroud with at least one through-hole, a shroud with at least one air scoop, or both. In additional examples, the method may comprise sequentially injecting additional samples into the gas chromatography system using a substantially constant injection-to-injection time. In some examples, the fan may be modulated at the second speed to reduce cool down time by at least 50-75% as compared to modulating the fan at the first speed. In other examples, opening of an air inlet aperture and an exhaust aperture during the cooling step, in combination with the fan modulation to reduce the cool down time by at least 50-75%, may be performed.

Additional aspects, features, examples and embodiments are described in more detail below.

BRIEF DESCRIPTION OF THE FIGURES

Certain aspects and examples are described in more detail below with reference to the accompanying figures in which:

FIGS. 7A-7C show various views of an embodiment of an oven comprising a recirculation path configured as a shroud with at least one through-hole, in accordance with certain examples;

FIGS. 29A-C are gas chromatograms showing performance of the oven when the column is in a front position and a back position, respectively, in accordance with certain examples.

Figure 1:
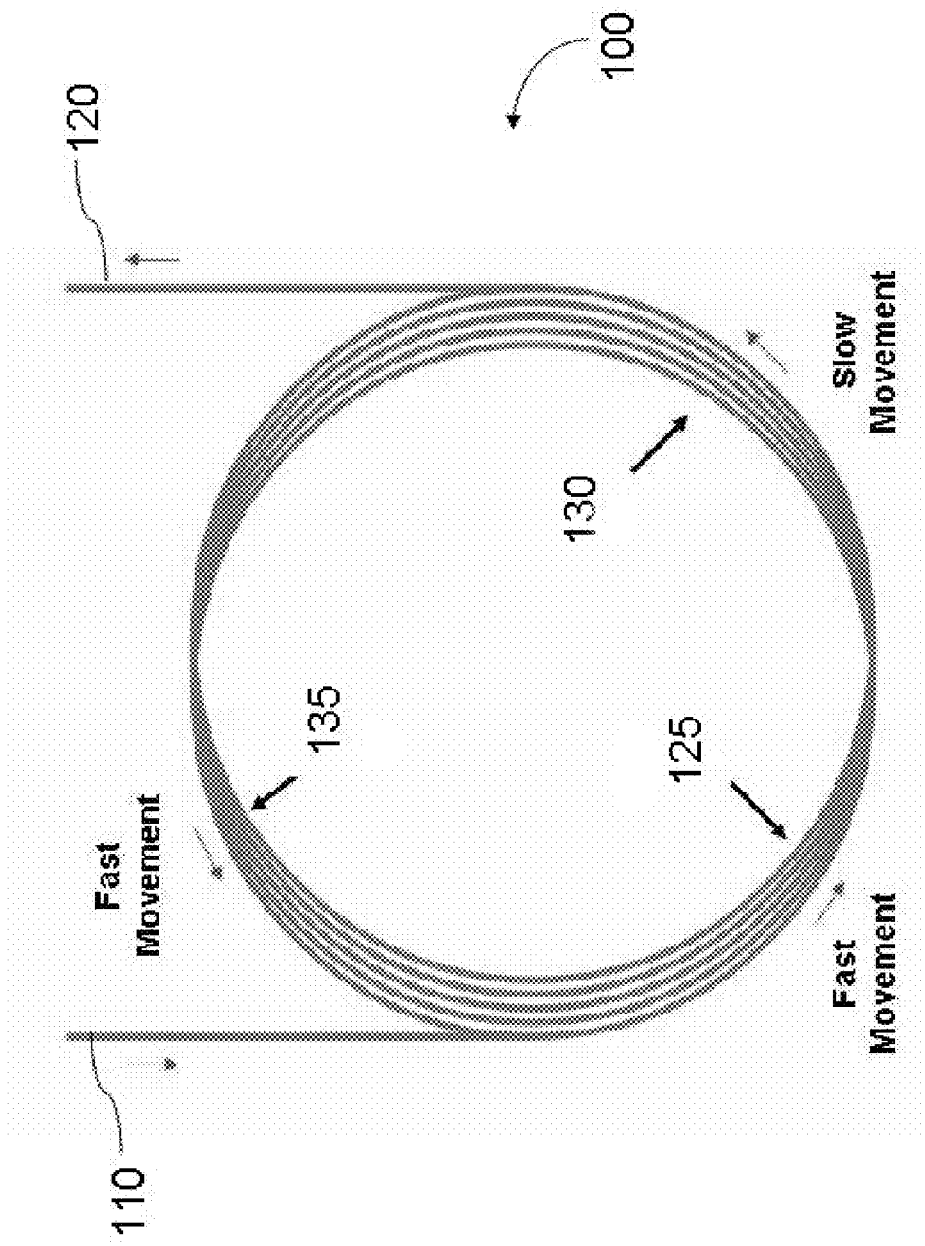
FIG. 1 is a schematic of a chromatography column, in accordance with certain examples.

It will be recognized by the person of ordinary skill in the art, given the benefit of this disclosure, that reference to the terms "top," "side," "bottom," "up" and "down" are for illustrative purposes only and do not limit the devices disclosed herein to any particular orientation, shape or structure. Also, certain dimensions or features in the figures may have been enlarged, distorted, altered or otherwise shown in a non-conventional manner to facilitate a better understanding of the technology.

DETAILED DESCRIPTION

Certain features, aspects and examples of the technology disclosed herein provide significant advantages over existing systems including, but not limited to, better temperature regulation, simpler operating parameters, less user input and the like.

Embodiments of the ovens disclosed herein generally include a housing that contains a heating element, a space to receive a device whose temperature is to be controlled and one or more fans. Depending on the exact oven design, the oven may further include a recirculation path, a programmable motor to modulate fan speed and/or a motor to adjust the position of an air intake and/or an air exhaust. These and other components of the oven are described in more detail below.

Certain embodiments disclosed herein are directed to an oven that is configured to provide a substantially constant temperature in a space in the oven. In certain embodiments disclosed herein, substantially constant temperature refers to a temperature that varies by no more than about 2-3° C., e.g., varies by 1° C. or less. The exact space in the oven where the temperature should be substantially constant may vary depending on the intended use of the oven. In chromatography applications, the space in the oven that has a substantially constant temperature may be at least the space occupied by a chromatography column. In non-chromatography embodiments, e.g., cooking, vapor deposition, semi-conductor processing applications and the like, the size of the space with the substantially constant temperature may vary. In some embodiments, the entire oven may have a substantially constant temperature.

It will be recognized by the person of ordinary skill in the art, given the benefit of this disclosure, that even though the space may have a substantially constant temperature, the temperature may not be substantially constant over time. For example, during a gas chromatography run, it may be desirable to ramp the temperature from a first temperature to a second temperature. The temperature of the space in the oven that is occupied by a chromatography column is substantially constant at the first temperature prior to the ramp. After the ramp, the space in the oven that is occupied by a chromatography column has a substantially constant temperature that is about the second temperature. Even though the temperature may periodically change, preferably the space occupied by different portions of a chromatography column are at substantially the same temperature to avoid aberrant effects that may arise from temperature differences in the column. These aberrant effects and devices and methods to avoid them are discussed in more detail below. It may also be desirable to operate the gas chromatography system at one or more temperatures during an analysis stage, e.g., a stage where species in a sample are separated, and to change the temperature back to a starting temperature during a cool down stage. As the system transitions from an analysis stage to a cool down stage, the temperature of the space occupied by the column may also change temperature such that the space occupied by the column has a substantially constant temperature after the cool down stage and/or during an analysis stage.

In accordance with certain examples, an oven comprising a recirculation path is provided. In certain examples, the oven may be used in a chromatography system to provide improved and more even temperature control particularly in the space occupied by a chromatography column. In other examples, the oven may be used in a non-chromatography setting to provide improved and more even temperature control. The oven may be used to provide a constant temperature or may be used to provide a temperature ramp, as discussed further below. In embodiments where the oven is used in a gas chromatography system, the oven may be particularly useful for analysis of petrochemicals, food, fragrances, environmental analyses, materials testing and other analysis where one or more volatile analytes are present. Additional uses, examples and devices using embodiments of the oven are disclosed in more detail below.

In accordance with certain examples, the ovens disclosed herein may be used in a gas chromatography system. Gas chromatography (GC) is a technique whereby volatile organic components in a sample may be separated and identified. In some examples, a fixed oven temperature may be used, whereas in other examples the oven temperature may be ramped such that different components in the sample vaporize at different times and temperatures. For example, a sample may be injected and the oven temperature may be increased over a temperature range that encompasses the boiling points of the components in the sample. As components are vaporized, these components are carried through a chromatography column. The components elute from the column at different times depending, at least in part, on the exact chemical makeup of the components in the sample and the material selected as the chromatography medium. As the components elute from the column, they may be detected using a suitable detector such as, for example, those illustrative detectors discussed herein. In certain instances, this detection may be output to a screen or printing device and is generally shown as a "peak" representative of elution of the component.

In certain examples, a conventional oven may provide inconsistent heating at various regions of a chromatography column. For example and referring to FIG. 1, a chromatography column 100 is shown as having an inlet 110 and an outlet 120. In a typical configuration used in gas chromatography, the column 100 is wound in a generally circular manner to provide increased length while reducing the amount of space occupied by the column. The temperature of a chromatography column, when placed in a conventional oven, may be different at different regions. This result can induce concentration gradients within the column which results in poor peak shape. For example, as a component in a sample enters the column 100, the uneven column temperature may cause the component to traverse different regions of the column at different speeds. At region 125 of the column 100, the component moves at a higher speed as compared to the speed at region 130 due to the temperature at region 125 being higher than the temperature at region 130. Similarly, the speed at region 135 is higher than the speed at region 130 due to the higher temperature at region 135 as compared to the temperature at region 130. This non-constant speed of the component through the column can cause the peaks to stretch and compress, which provides poor peak shape that makes it more difficult to accurately quantify how much of each component is present in a sample. This effect may be worse with thin-film columns with overloaded peaks and with slow temperature ramping.

Figure 2:
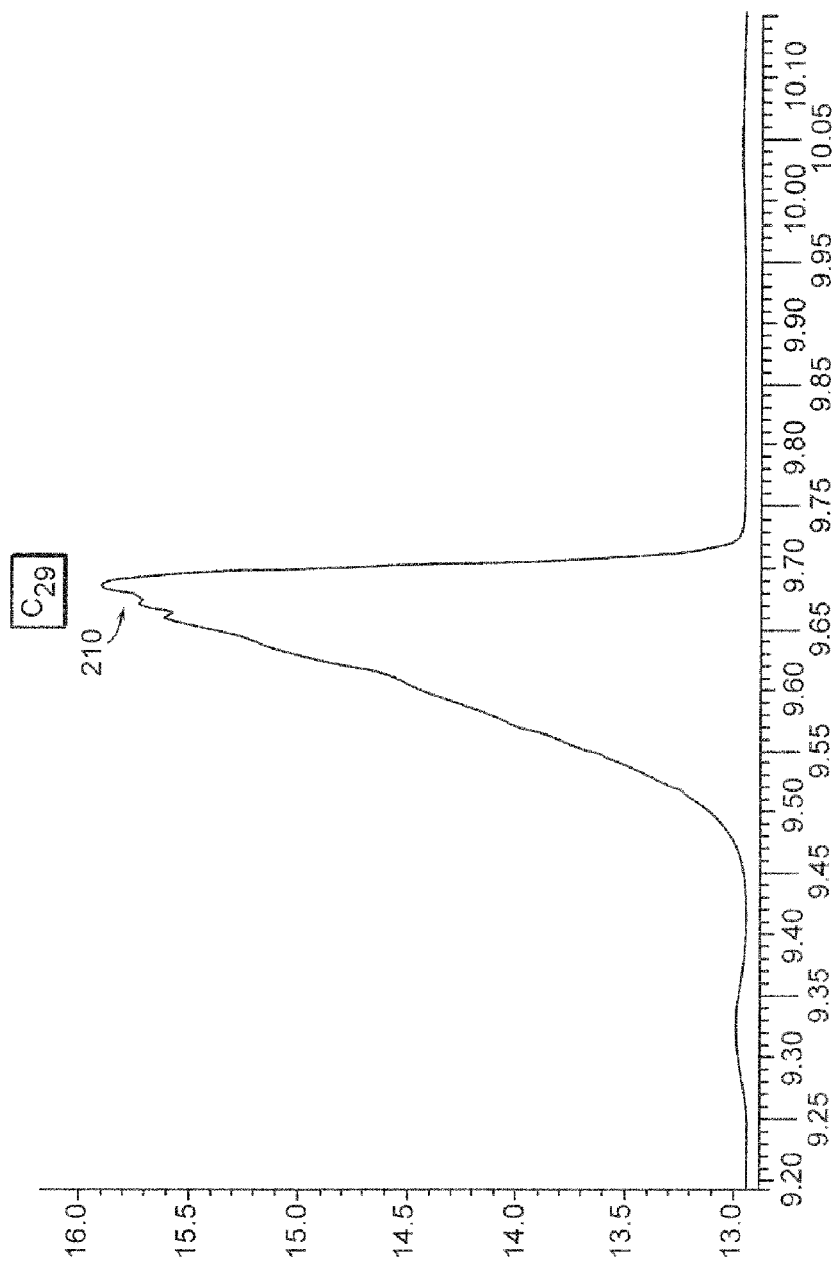
FIG. 2 is a gas chromatogram showing a Christmas tree effect, in accordance with certain examples.
Figure 3:
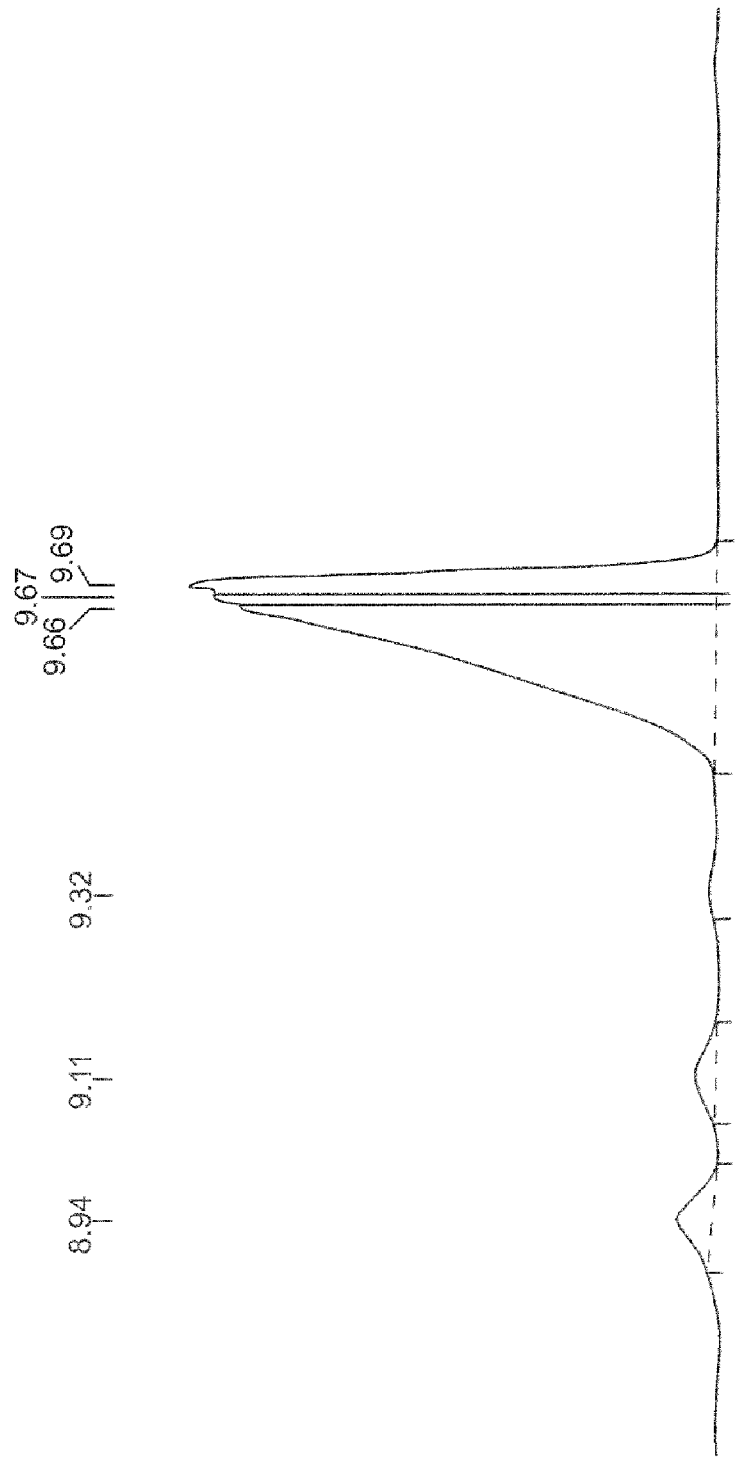
FIG. 3 is a processed version of the gas chromatogram of FIG. 2, in accordance with certain examples.
Figure 4:
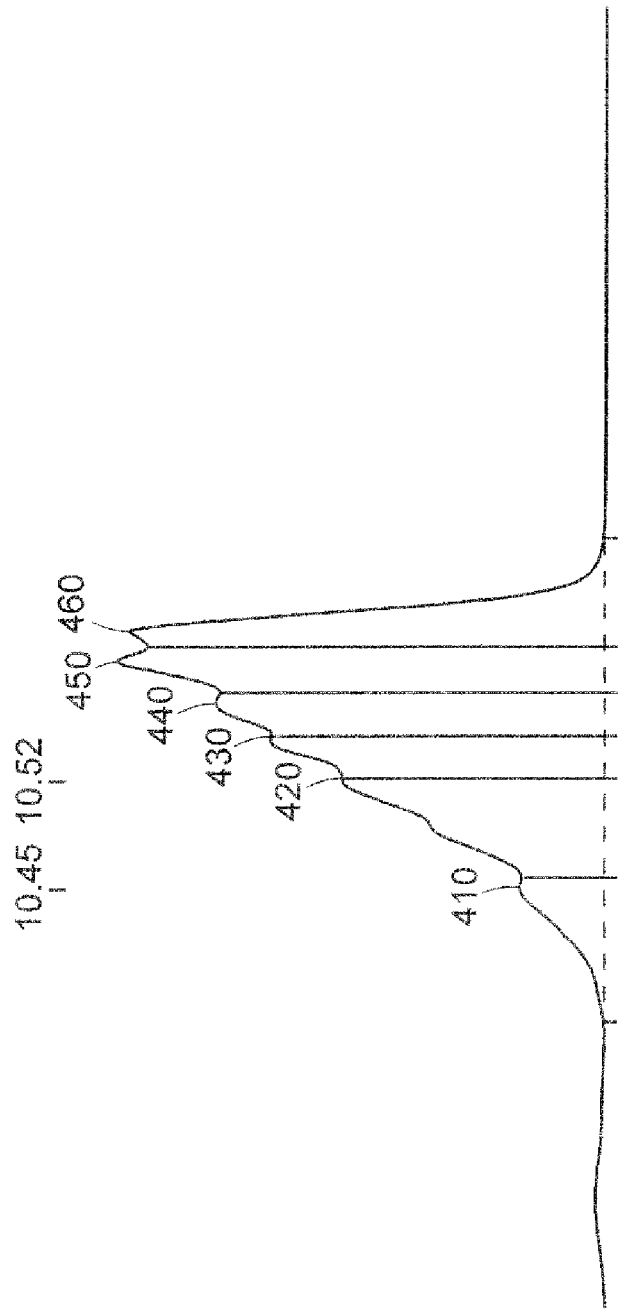
FIG. 4 is a gas chromatogram showing an extreme Christmas tree effect, in accordance with certain examples.

In certain examples, a result of this temperature differential in the chromatography column is appearance of a Christmas tree effect. An illustration of this Christmas tree effect is shown in FIG. 2. The chromatogram shown in FIG. 2 was obtained by injecting a 5% w/v solution of paraffin wax in toluene into a typical gas chromatograph having a 15 m×0.250 mm×0.1 µm 5% phenyl/dimethylpolysiloxane column. The flow rate of carrier gas helium was 1.0 mL/min. The starting temperature was 220° C. for 1 minute, and then the temperature was ramped to 280° C. at 2.5° C./min. As the hydrocarbon (C29) entered the gas chromatograph, the temperature differential in the column caused broadening of the peak 210 and provided a peak having shoulders. This poor peak shape may make it difficult to accurately quantify the concentration of the species present, which is typically measured as the area under the curve. For example and referring to FIG. 3, in automated processing of the peak 210, the software of the analysis system may inaccurately identify the peak 210 as a mixture of several peaks or may incorrectly identify one of the shoulders as the primary peak maximum. These errors can lead to inaccurate identification of the amount or percentage of a component present in the sample. In extreme cases, a single species eluting from the column may be identified by the analysis software as a plurality of peaks. An example of this is shown in FIG. 4. A single component has eluted from a gas chromatography column and has a Christmas tree shape. During analysis, the software of the analysis system identifies the single peak as being six different peaks, 410, 420, 430, 440, 450 and 460. This aberrant result may make quantification of this component difficult.

In certain examples, embodiments of the oven disclosed herein may be constructed and arranged to provide a substantially constant temperature to a chromatography column. While the temperature of the oven may or may not be constant, e.g., the oven may be operated at a single temperature or may ramp the temperature from a first temperature to a second temperature or more, the temperature of substantially all regions of the chromatography column may be at about the same temperature. As discussed further below, such even temperatures may be provided through the use of a devices and methods to circulate air in the oven to reduce the likelihood that hot and cold spots are present in or near the chromatography column.

Figure 5:
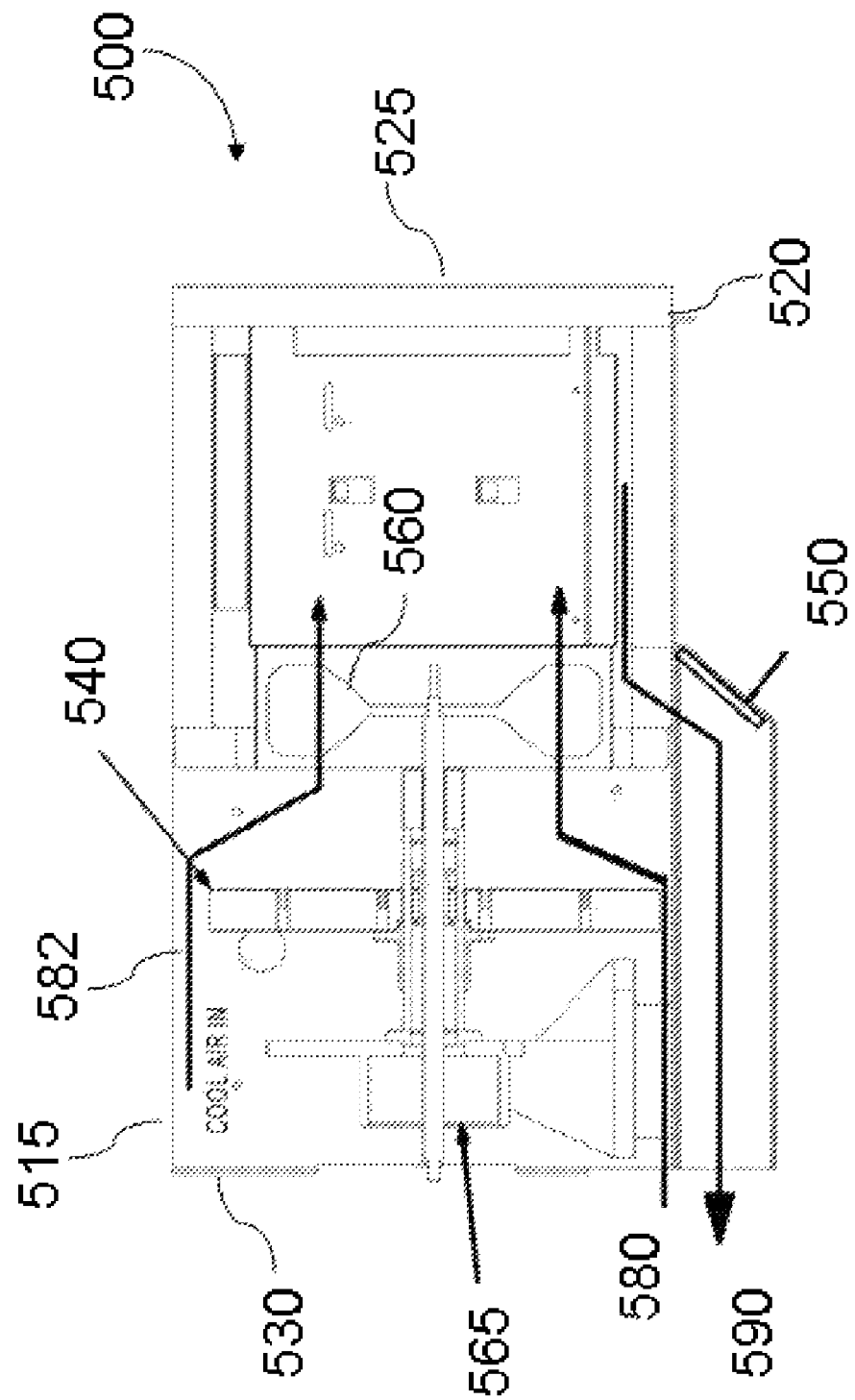
FIG. 5 is an embodiment of an oven, in accordance with certain examples.

In accordance with certain examples, an example of an oven constructed and arranged to provide a substantially constant temperature to a chromatography column is shown in FIG. 5. The oven 500 generally includes a housing having a top 515, bottom 520 and sides 525 and 530. The oven 500 includes an air intake aperture 540, which may take the form of a port or a door, and an air exhaust aperture 550, which may also take the form or a port or door. Both the air intake aperture 540 and the air exhaust aperture 550 are shown in an open position in FIG. 5 to draw air into or exhaust air from the oven. The oven 500 may also include a fan 560 that is operated by a fan motor 565. During operation of the oven, air may be drawn into the oven 500 through the air intake aperture 540, as shown by arrows 580 and 582, by switching the fan 560 on. Air may also be exhausted from the oven 500 through the air exhaust aperture 550 as shown by arrow 590.

In some examples, the oven may include a single air intake aperture and a single exhaust aperture, whereas in other examples two or more air intake apertures and/or two or more air exhaust apertures may be present. The exact position of the air intake aperture and the air exhaust aperture may vary, and in certain examples, the air intake may be positioned on a top surface of the oven and the air exhaust aperture may be positioned on a bottom surface of the oven. A fluid flow path operative to couple the air intake aperture and the air exhaust aperture may be present in the oven such that ambient or cooling air is drawn into the oven through the air intake aperture, receives heat from the oven, and is expelled as hot air from the air exhaust aperture. One or more ports, ducts or channels may be fluidically coupled to the air intake aperture and/or the air exhaust aperture to carry the air into and out of the oven.

Figure 6:
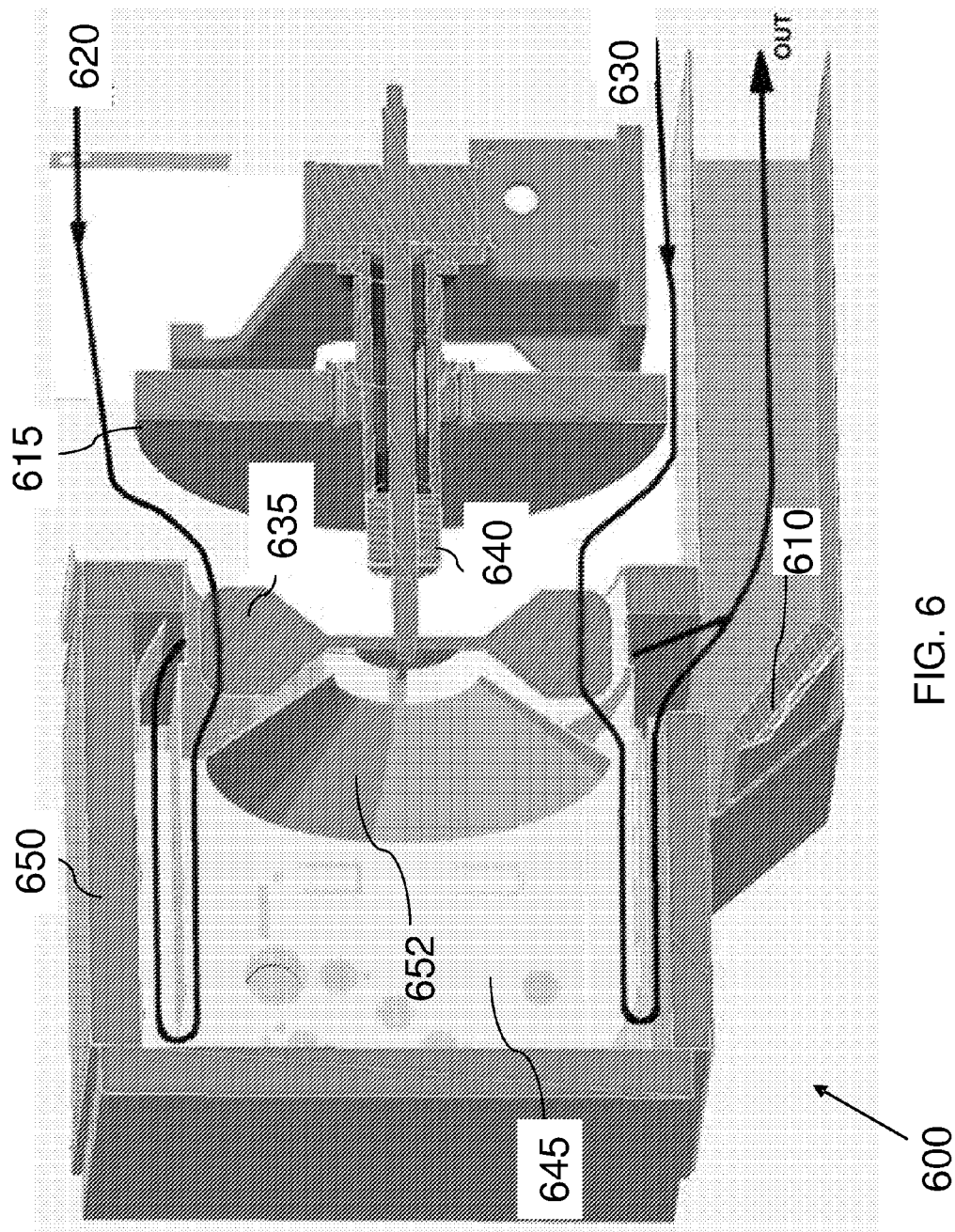
FIG. 6 is another embodiment of an oven, in accordance with certain examples.

In certain examples, the oven itself may be constructed and arranged such that the oven may be vented rapidly to reduce the temperature of the oven to ambient temperature (or some other desired temperature). An example of a double-walled oven is shown in FIG. 6. The double-walled oven 600 comprises an air exhaust aperture 610 on a bottom surface of the oven 600. Heated air may be expelled from the oven by opening the air exhaust aperture 610. Ambient air may be drawn into the oven by opening an air intake door 615, which permits cooling air to enter the oven as shown by arrows 620 and 630. A fan 635, powered by a motor 640, may be switched on to aid in drawing air into the oven to cool the oven. The air intake aperture is typically mounted behind and concentric to the fan 635 to draw air into the oven. As air enters the oven, it may pass between an inner wall 645 and an outer wall 650 in the oven 600. The inner wall surrounds a heat structure support 652 which is configured to receive a heating element. The inner wall also typically surrounds the chromatography column and may include one or more ports to provide for coupling of the column to a detector and/or a sample introduction device. The outer wall 650 may be effective to reduce the heat loss during heating of the oven, which may improve the heating rate and may reduce non-uniform temperatures in the column. This double-walled oven configuration provides for the cooling air to pass over an increased amount of heated surface area of the inner chamber to draw heat away from the oven in a rapid manner. The exact space between the inner wall 645 and the outer wall 650 may vary, and in certain examples, there is an air gap of about 0.5 to 1.5 inches, more particularly about 0.75 to 1.25 inches, e.g., about 0.75 to about 1 inch of space between the inner wall and outer wall. It will be recognized by the person of ordinary skill in the art, given the benefit of this disclosure, that the space between the inner and outer walls may take other sizes depending at least in part, on the overall size of the oven.

In certain examples, the position of the air intake aperture and the air exhaust aperture may be controlled by sending a suitable signal from a controller. Each of the air intake aperture and the air exhaust aperture may be coupled to a motor such that the aperture may be opened or closed, at least to some extent. The motor may be actuated in response to a signal to close the air intake and exhaust apertures during an analysis and to open the air intake and exhaust apertures during cool down. Illustrative motors include a stepper motor, a piezoelectric motor, a brushed DC motor, a brushless DC motor, an AC motor, an asynchronous AC motor, or a servo drive DC motor with sensor feedback for position on either motor or actual door position. Other position control devices may also be used. In examples where a DC or AC motor is used, it may be desirable to include a resolver or encoder to provide position feedback.

In accordance with certain examples, during operation of the oven, the air intake apertures(s) and air exhaust apertures(s) may be closed to prevent air from entering into the oven. The fan may be used to circulate air through the oven to reduce temperature gradients in the chromatography column. In certain examples, as discussed in more detail below, the oven may be configured with a recirculation path to circulate air and further reduce the likelihood that temperature gradients in the column will arise. In other examples, the speed of the fan may be modulated, either during analysis, during cooling or both, to further increase the overall operating efficiency of the oven. In some examples, a recirculation path is present and the fan speed may be modulated. Additional embodiments using a recirculation path and/or modulation of fan speed are described below, and other suitable embodiments will be readily selected by the person of ordinary skill in the art, given the benefit of this disclosure. Embodiments that include a recirculation path, a fan whose speed is modulated, or both may permit cooling of the oven from about 350° C. to about 50° C. in about one minute, or from about 450° C. to about 30° C. in four minutes or less. In certain embodiments, this rapid cooling may provide a 50-75% decrease in the time required to cool the oven back to a starting temperature of 30° C. of less when compared to existing ovens used in gas chromatography, e.g., ovens whose fan speeds are not modulated.

In accordance with certain examples, the ovens disclosed herein may include a recirculation path. A recirculation path provides for increased mixing of air downstream and upstream from the fan such that a more even temperature may be present in the oven, e.g., the recirculation path provides for more air flow around the fan blades, mixing of air on both sides of the fan blades, or both, to improve air circulation in the oven. In some examples, the recirculation path may include one or more through-holes in a shroud to connect the air inlet and the air exhaust to improve air circulation. In other examples, the recirculation path may include one or more air scoops constructed and arranged to facilitate passage of air to the fan. In some examples, the recirculation path may include a shroud with one or more through-holes in combination with one or more air scoops. Other configurations are possible and will be recognized by the person of ordinary skill in the art, given the benefit of this disclosure.

Figure 7C:
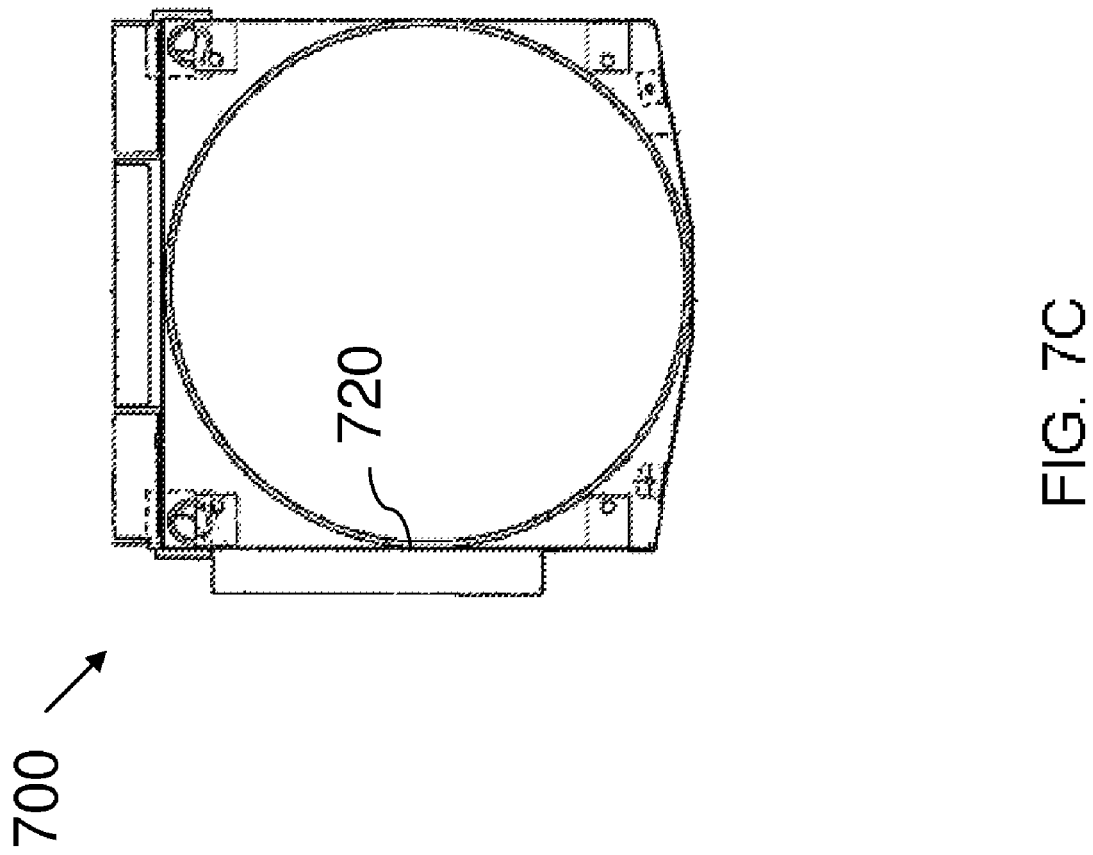

In certain examples, a shroud comprising one or more through-holes that are constructed and arranged to provide for mixing of air within the oven to reduce the likelihood of temperature gradients is provided. One example of a recirculation path is shown in FIGS. 7A-7C. Referring to FIG. 7A a perspective view of an oven is shown. The oven 700 generally comprises a housing 710, which is shown as being substantially square though other shapes are possible. A recirculation path 720 in a shroud comprises a plurality of through-holes, such as, holes 722 and 724 shown in the top view of FIG. 7B. The shroud 720 is configured to be inserted into the front of the oven 700 to provide air exchange between the air inlet and air exhaust. In some examples, the shape and profile of the shroud does not substantially alter the inner diameter of the oven, as seen through the back view of the oven 700 shown in FIG. 7C. By not altering the inner diameter of the oven, existing columns, injectors, detectors and the like may be used without modification. In addition, certain embodiments of the shroud do not substantially alter the overall dimensions of the oven.

In embodiments where a shroud comprising through-holes is used to provide a recirculation path, the exact number and shape of the through-holes in the shroud may vary. In certain examples, the holes may have a shape that is circular, rectangular, elliptical, trapezoidal, hexagonal, octagonal, triangular and the like. The holes may take any shape that permits recirculation of air. The exact number of through-holes may vary and in some examples, the number of through-holes is one, two or more, e.g., four or more. In certain examples, the through-holes may be spaced evenly around the circumference of the shroud, whereas in other examples, the through-holes may be grouped on one surface, e.g., a top surface, of the shroud. In some examples, the holes may be produced in the shroud by drilling, machining, cutting or otherwise removing a desired amount and shape of material from the shroud to provide one or more openings in the shroud. In certain examples, the shroud may be sized and arranged to be inserted and held in a front part of an oven to provide the air circulation, e.g., the shroud may be friction fitted, riveted, welded or held by integrating a fastener such as a tab into the shroud to attach the shroud to the oven. Other embodiments of a shroud comprising one or more through-holes to provide increased air circulation will be recognized by the person of ordinary skill in the art, given the benefit of this disclosure.

Figure 8B:
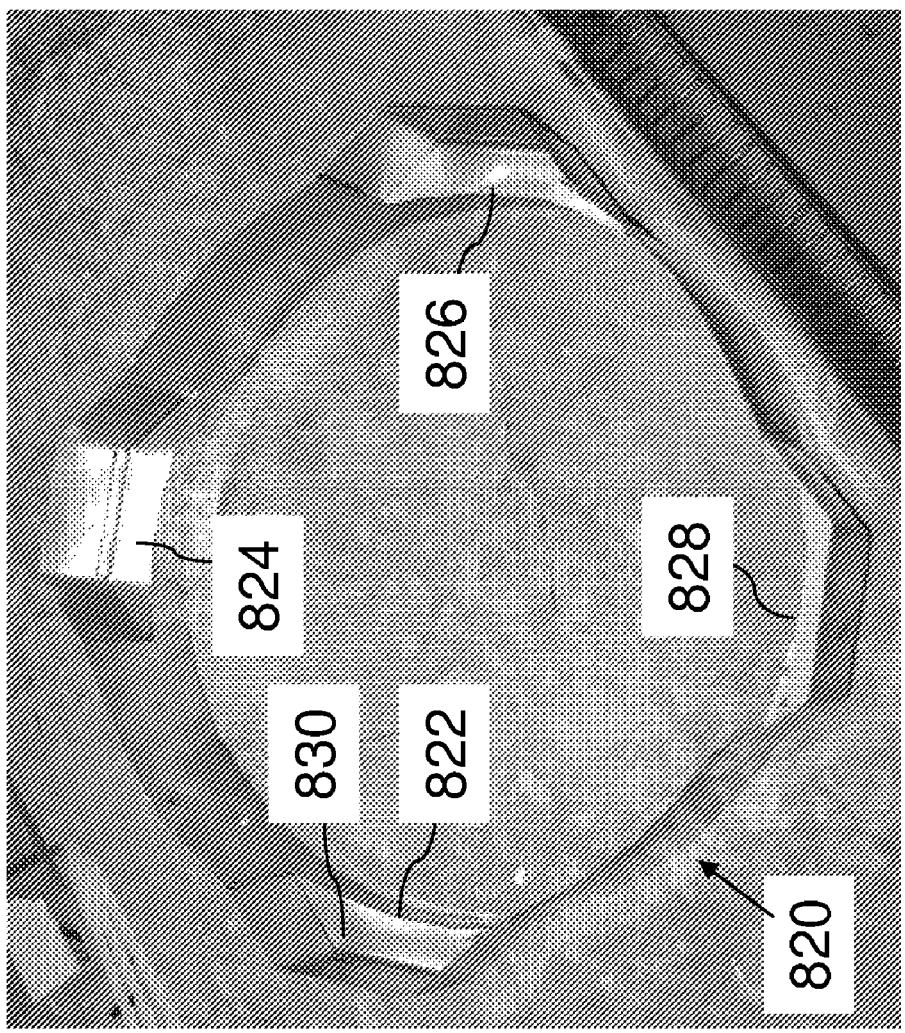
FIGS. 8A-8B show embodiments of a shroud comprising an air scoop, in accordance with certain examples.
Figure 8A:
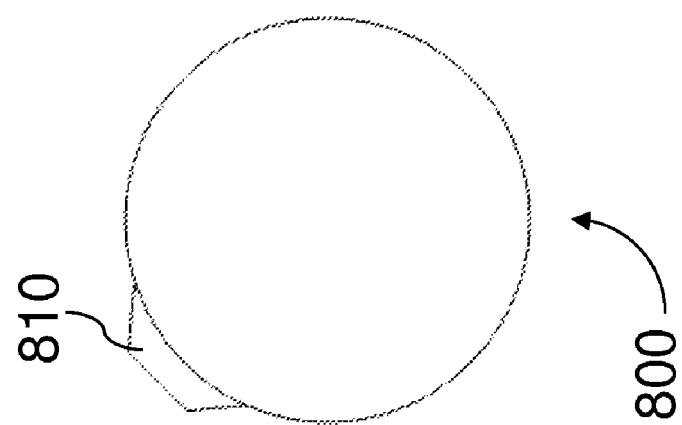

In accordance with certain examples, a top view of a recirculation path that is configured as an air scoop is shown in FIG. 8A. The air scoop 810 is integrated into a corner of the shroud 800. The shroud has a generally circular body, and the air scoop 810 is integral with the shroud 800, though it may be separately manufactured and coupled to the shroud 800 through a suitable fastener or adhesive. A fan (not shown) may be mounted within the shroud and may be sized and arranged such that it may freely spin within the shroud 800 without hitting the surfaces of the shroud 800. In certain examples, the largest fan size that may be operated without striking the shroud surfaces may be used to provide for increased air circulation. By selecting such a large fan, air entry behind the fan blades may be limited due to the limited space between the fan blades and the shroud. The air scoop 810 shown in FIG. 8 takes the form of a trapezoidal-shaped projection extending radially from the shroud 800. The air scoop 810 may be constructed and arranged to permit entry of air to the back of fan blades (not shown) to increase circulation of the air by the fan. Without the use of an air scoop, a large fan may function more like a paddle and provide poor air circulation, which can create uneven temperatures in the oven.

In certain examples, the exact number of air scoops included in the shroud may vary and in certain examples, one, two, three, four or more air scoops may be included. For example and referring to FIG. 8B, a photograph showing a perspective view of a shroud 820 that includes four air scoops, 822, 824, 826 and 828 is shown. The air scoops 822-826 may be positioned at the corners of the shroud 820 in a generally symmetrical manner about a central axis of the shroud 820. In some examples, however, the air scoops may be positioned asymmetrically in the shroud. As shown in FIG. 8B, the air scoops may include a generally flat surface, such as surface 830, which can assist in creating turbulence to enhance circulation of air within the oven. In some examples, one or more through-holes may be provided in the flat surfaces or in the shroud to increase circulation of air even further.

Figure 8C:
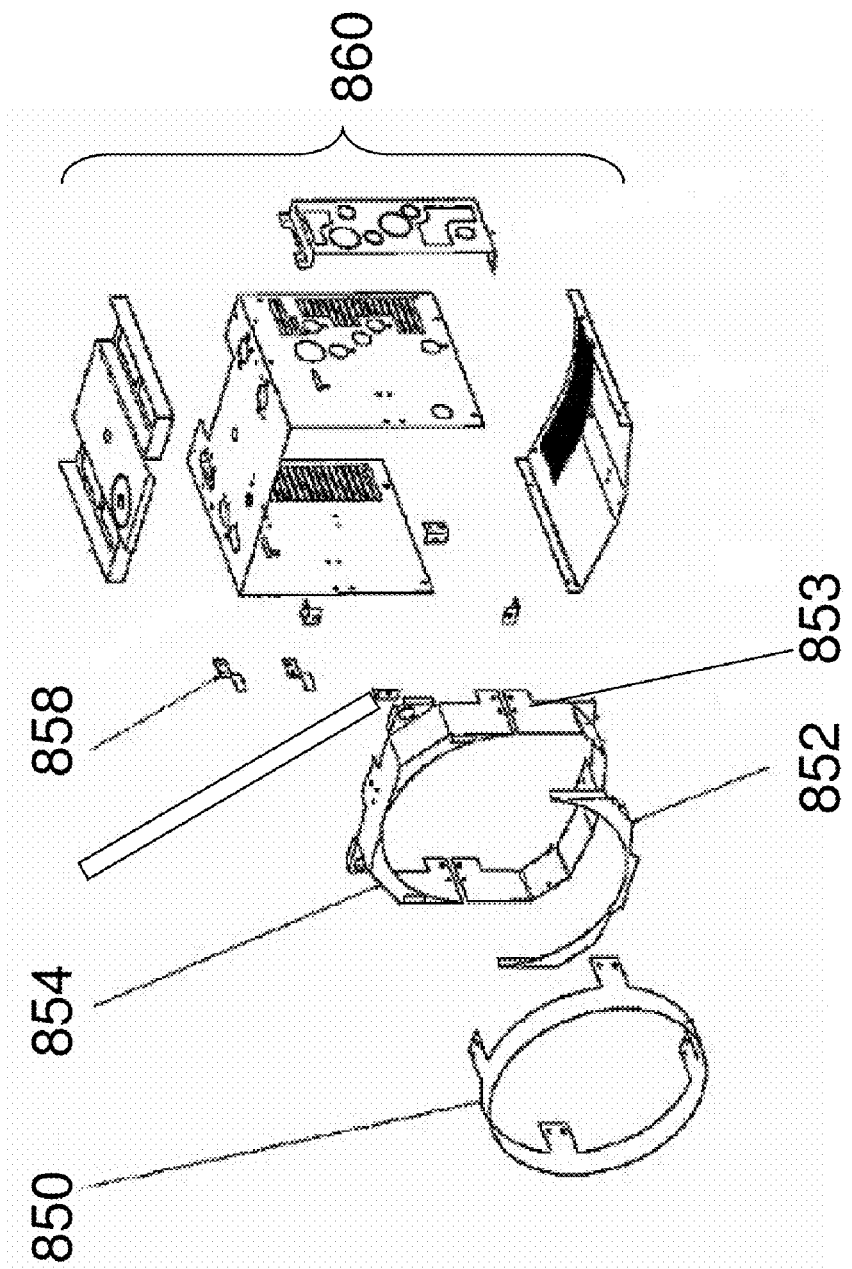
FIG. 8C shows a perspective view of an oven comprising a shroud with an air scoop in each corner of the shroud, in accordance with certain examples.

In some examples, the air scoops may be a multiple component device that is held in place in the oven. An example of this is shown in FIG. 8C. The air scoop includes three different components 852, 853 and 854 that couple with a circular shroud 850 to provide a transition from the circular shroud to a rectangular oven liner. The oven includes a housing 860, which is shown in FIG. 8C in an exploded view. One or more fasteners or tabs, such as tab 858 are operative to hold the air scoop/shroud assembly in the oven. It will be within the ability of the person of ordinary skill in the art, given the benefit of this disclosure, to select additional ways of assembling an air scoop and mounting such air scoop in an oven.

Figure 9A:
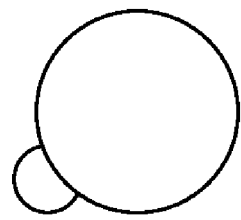
FIGS. 9A-9F show various air scoop shapes, in accordance with certain examples.
Figure 9B:
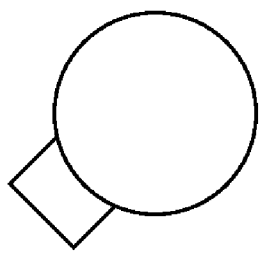
Figure 9C:
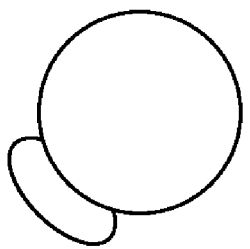
Figure 9D:
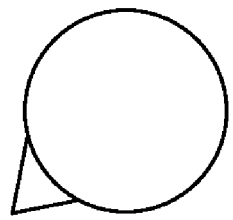
Figure 9E:
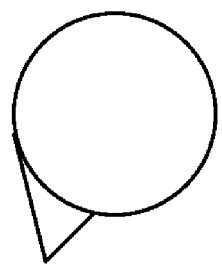
Figure 9F:
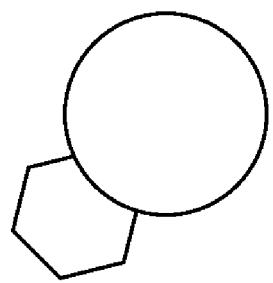

In accordance with certain examples, the exact shape and size of the air scoops may vary. In certain examples, the shape of the air scoops may be semi-circular (FIG. 9A), rectangular (FIG. 9B), elliptical (FIG. 9C), triangular (FIGS. 9D and 9E), trapezoidal, hexagonal (FIG. 9F) or may take other shapes. The size or dimensions of the air scoops may also vary and preferably the scoops have suitable dimensions to provide for mixing of air in the oven while not being too large such that the oven dimensions must be substantially altered to accommodate the shroud including the air scoops. It will be within the ability of the person of ordinary skill in the art, given the benefit of this disclosure, to design and use shrouds having a suitable type and number of air scoops to increase air circulation within an oven.

In accordance with certain examples, the nature and type of materials used to make the air scoops may vary and, in some examples, any material may be used that can withstand the oven temperatures. In certain examples, the air scoop may be produced using the same material as the shroud to avoid any differences in thermal expansion as the oven is heated, whereas in other examples, the shroud and air scoop may be produced using different materials. Illustrative materials for use in producing the air scoop(s) include, but are not limited to, steel such as stainless steel, metals such as aluminum, titanium and the like, high temperature polymers, and ceramics, and additional suitable materials will be readily selected by the person of ordinary skill in the art, given the benefit of this disclosure.

In certain examples, the oven may be configured with a fan that is driven by a programmable DC motor. In existing ovens used in chromatography systems, the fan is typically operated at a fixed speed during analysis and during cool down. Embodiments of the oven disclosed herein include a fan whose speed may be modulated or altered continuously or intermittently. For example, the fan speed may be operated at 1400 rpm during analysis and the fan speed may be increased, e.g., to about 2800 rpm, during cool down to increase the rate at which the oven is cooled to a starting temperature. In some examples, the oven may include a single fan fluidically coupled to the air inlet and air exhaust, whereas in other examples, each of the air inlet and the air exhaust may include its own fan whose speed may be modulated to provide further control in adjusting the temperature within the oven.

In accordance with certain examples, cooling of the oven down to a starting temperature may be accomplished by opening the air inlet and the air exhaust to provide air flow between ambient air and the internal oven area. A fan in the oven is operative to increase the amount of ambient air inside the oven by drawing ambient air through the air inlet duct and exhausting the hotter oven air out the air exhaust to cool the oven. Some existing ovens accomplish the cooling using an external fan to force ambient air through an air inlet duct and out an air exhaust duct. The inlet and exhaust ducts are typically opened at a defined time using some electro-mechanical control such as a stepper motor. When cool down is requested by the system, these inlet and exhaust ducts are typically opened fully until the oven cools to the new requested oven temperature as sensed by a temperature sensor (usually a platinum resistance thermometer) located within the oven. Such systems may be more complex and costly.

In certain examples, the temperature of the ovens disclosed herein may be controlled by continuously or intermittently modulating a speed of the fan. By altering the fan speed during analysis, increased air circulation may be provided within the oven to reduce the likelihood of temperature gradients within the oven. Similarly, the fan speed may be modulated during cool down to increase cooling thus reducing the injection-to-injection time in a chromatography system that includes such an oven. Modulating the fan speed may also provide for a user defined temperature profile, e.g., a user defined heating rate or a user defined cooling rate.

Figure 10:
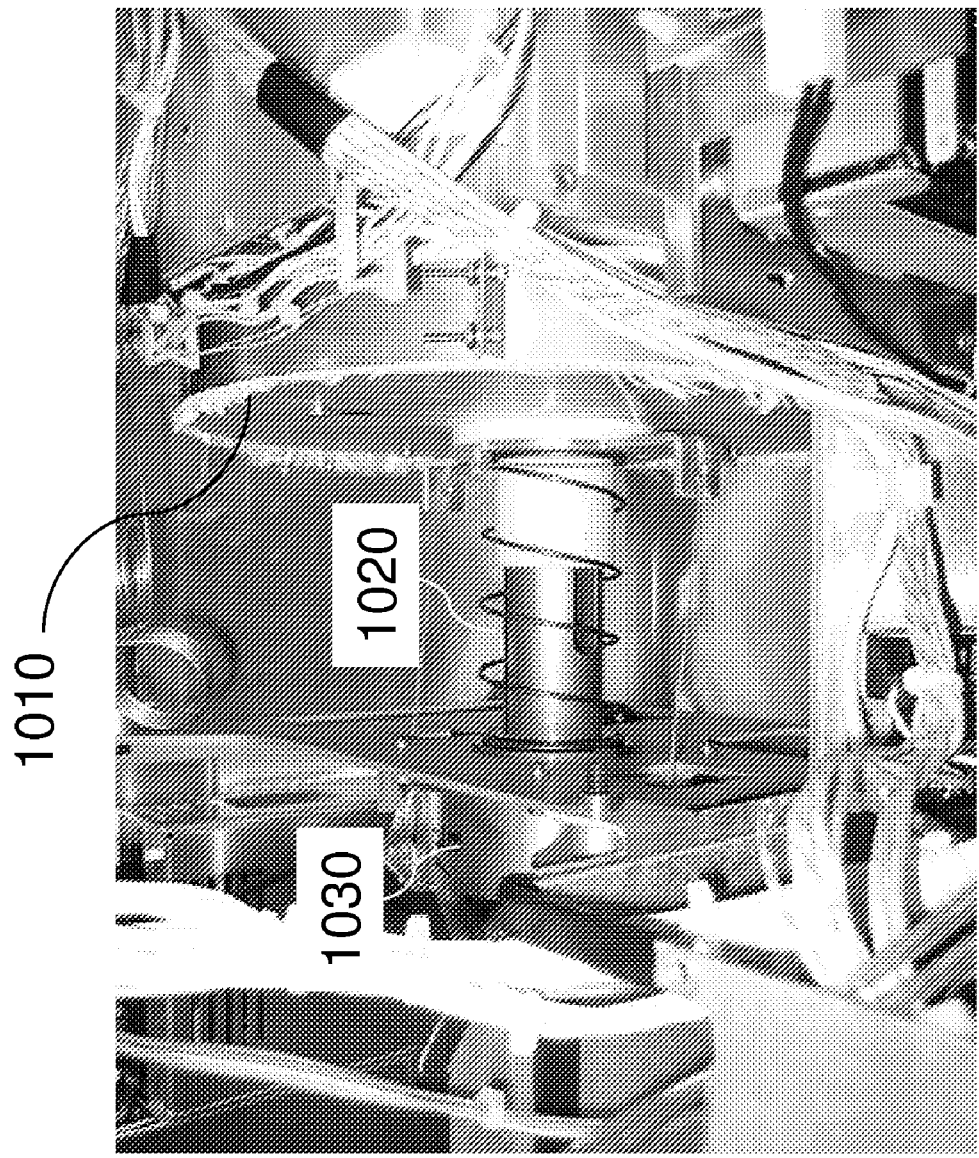
FIG. 10 is a photograph showing a top view of an air intake aperture of an oven, in accordance with certain examples.
Figure 11:
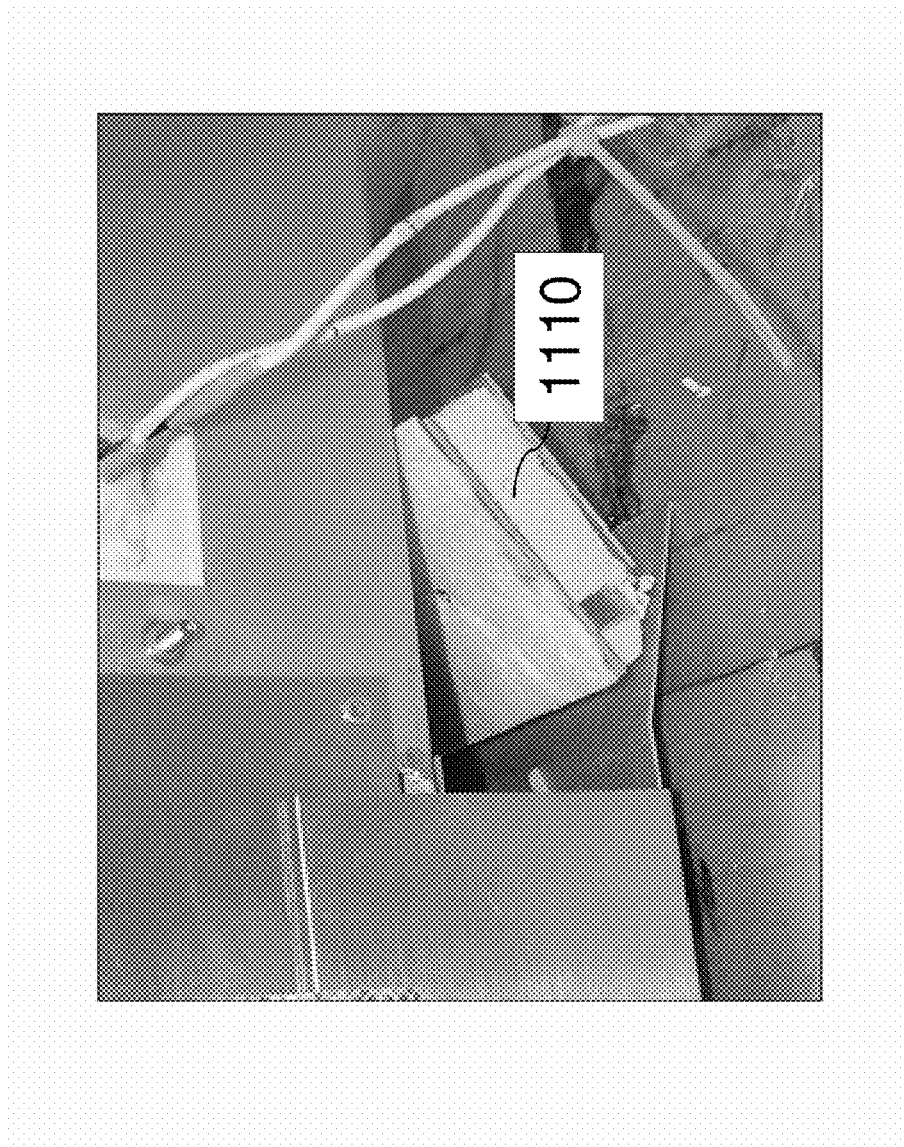
FIG. 11 is a photograph showing a side view of an air exhaust aperture of an oven, in accordance with certain examples.

In accordance with certain examples, a position of an aperture or door of the air inlet and/or the air exhaust may also be adjusted or modulated to further assist in temperature control in the oven. By adjusting the aperture position of the air intake and/or the air exhaust, the amount of ambient air that may pass into the oven may be controlled such that the oven follows a user defined temperature profile, e.g., a user defined heating rate or a user defined cooling rate. Referring to FIG. 10, a photograph of a fully open air intake door is shown. The position of the air intake door 1010 may be adjusted from fully open to fully closed (or any position in between) by a linkage 1020 to a motor 1030. The motor is typically a programmable DC motor to provide programmable control of the air intake aperture position. Similarly, a programmable DC motor may be coupled to the air exhaust aperture to modulate the position of the air exhaust aperture. For example and referring to FIG. 11 where a photography of an air exhaust aperture is shown, the air exhaust aperture may include an insulated flap 1110 whose position may be modulated during analysis and/or during cool down.

In certain examples, the actual oven cooling rate (or heating rate) may be measured by comparing sequential readings on a standard oven temperature sensor. The error signal between the user defined rate and the actual rate may be used in, for example, a conventional proportional integral control to drive a motor or motors (one for the air inlet aperture and a second one for the air exhaust aperture) which in turn continuously modulate the position of the apertures of the air inlet and the air exhaust. It should be understood that at a fixed oven fan speed, the more open the inlet and exhaust ducts are, the less the pressure drop will be within these ducts, and therefore more cooling air will flow through these ducts into the oven.

In certain embodiments, firmware may linearly link the oven fan speed to the oven inlet vent position such that when the air inlet aperture is fully open (e.g., 1100 steps of an inlet duct stepper motor) the fan speed goes to a maximum, (e.g., 2800 RPM, 4000 RPM, etc.), and thereafter the fan speed may linearly decrease with decreases in the inlet duct stepper motor position until the fan speed achieves a lower, or lowest, operating speed (e.g., 1400 RPM) when the inlet duct stepper motor is at a corresponding level (e.g., 400 steps open). It will be understood by the person of ordinary skill in the art, given the benefit of this disclosure, that for a fixed opening of the inlet and exhaust apertures, as the oven fan speed is increased, the pressure drop between the inner oven and outside ambient air changes such that more cooling air will flow through these ducts into the oven.

In some examples, a position of an air inlet aperture may be continuously adjusted while the position of an air exhaust aperture remains fixed in an open position. Similarly, a position of an air exhaust aperture may be continuously modulated while the position of an air inlet aperture remains fixed in an open position. Also, both the position of the air inlet and air exhaust apertures may be modulated to provide for user-defined heating or user-defined cooling. In certain examples, the position of the air inlet aperture may remain fully open for a first period and then may be modulated for a second period to a partially or fully closed position. Similarly, the position of the air exhaust aperture may remain fully open for a first period and then may be modulated for a second period to a partially or fully closed position. In some examples, the position of one or more of the air inlet aperture and the air exhaust aperture may each be adjusted between a fully open position and a fully closed position at a selected frequency such that the apertures are operative as if they are open for some period.

In accordance with certain embodiments, the ovens disclosed herein may be cooled down with less ambient noise than the amount of noise that is produced during cooling of ovens in a conventional manner. For example, certain examples disclosed herein may reduce the oven's audible noise. A problem with conventional ovens in chromatography systems such as, for example, gas chromatographs, is that when they enter cool down, the ambient audible noise is often very loud for a long period and a problem for nearby instrument operators. Using the methods disclosed herein, the oven may be cooled in a rapid manner to reduce the time at which substantial ambient noise is produced.

In certain examples, the cool down rate control provided by the modulation of the air inlet and/or air exhaust apertures and/or the fan speed may improve the repeatability of the cool down time and therefore improve the precision of the injection-to-injection time which is important particularly where automated sample loading occurs. Further, by using the cool down rate control with an oven comprising a recirculation path, better temperature control along with reduced cool down time may be achieved to provide for increased sample throughput.

In certain examples, modulation of the fan speed and/or air apertures may provide for improved cooling after a temperature ramp. In conventional gas chromatography (GC) systems, the length of cool down time is determined in part by the past thermal history of the oven because the oven wall insulation stores residual thermal energy for over an hour. A typical GC method for a GC run might drive the oven temperature from about 50° C. to about 350° C. at a rate of about 20° C. per minute and then cool back to 50° C. before starting the next run. During this run, some of the oven's thermal energy is stored in the oven wall insulation. During subsequent runs, using the same method, more and more energy is stored in the oven wall insulation until some steady state value is reached after several hours. When the GC enters cool down during each run, this energy that is stored in the oven wall insulation leaks back into the oven and must be removed to achieve the final desired oven temperature. Since this stored thermal energy varies with each GC run, the amount of time to remove it also varies with each run. The magnitude of the problem depends on the final oven temperature that is desired with lower final temperatures presenting more of a problem. Embodiments disclosed herein that include one or more of a recirculation path, fan modulation or air intake and exhaust aperture adjustment may provide an oven that cools at a known rate to reduce the uncertainty in oven cooling from run to run.

Figure 12:
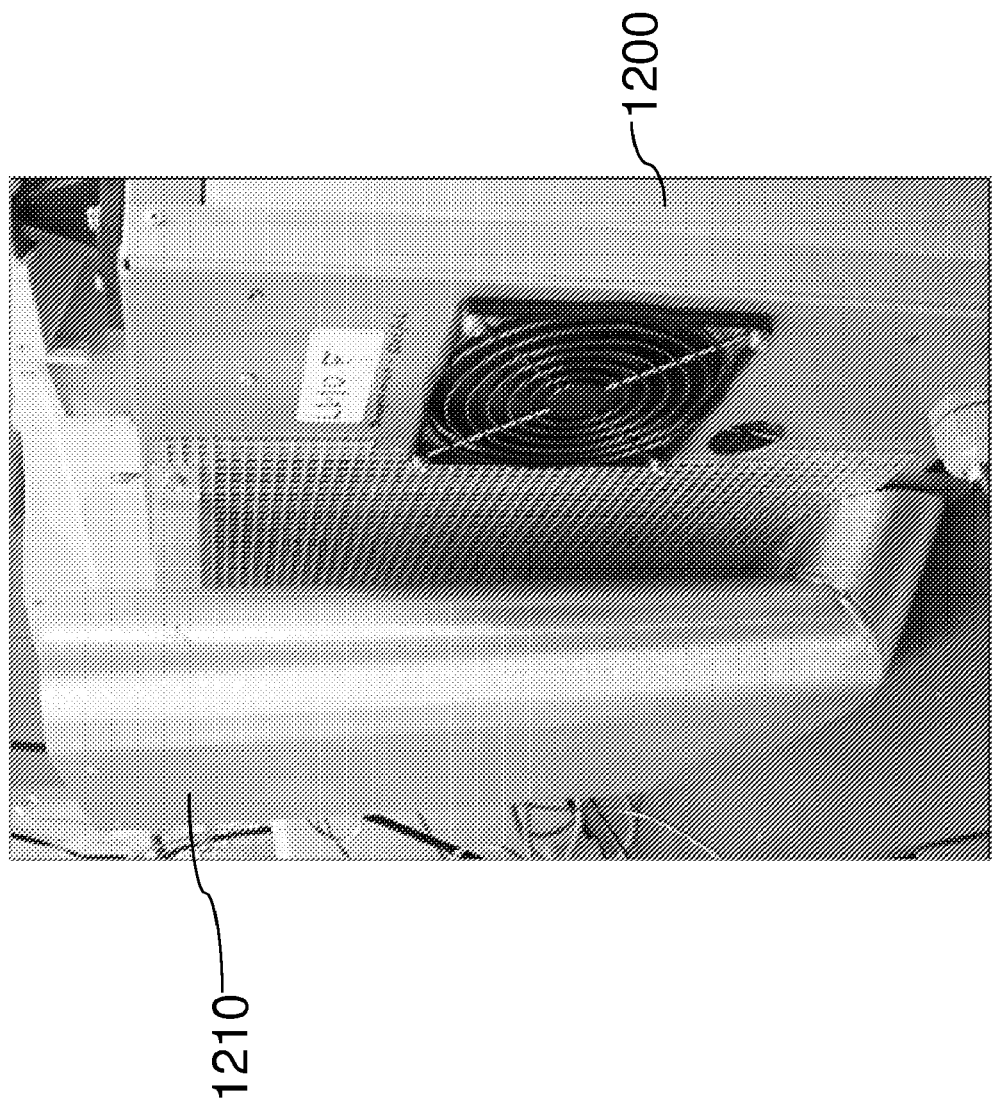
FIG. 12 is a photograph showing a vent coupled to an air exhaust aperture of an oven, in accordance with certain examples.

In certain examples, the oven disclosed herein may include a vent or pipe fluidically coupled to the air exhaust to route or provide a path for hot air to move away from the oven. A photograph showing such vent is shown in FIG. 12. The oven 1200 includes a vent 1210 that is fluidically coupled to the air exhaust aperture. In instances where the oven is placed against a wall, it may be difficult to remove the vented hot air from the oven surrounding due to poor air flow around the outside of the oven. The vent 1210 may be configured such that hot oven exhaust air may pass out of the top of the oven at a height such that the heated air is unlikely to be drawn back into the air inlet aperture of the oven. Such design may reduce cool down time and portability of the ovens, and may reduce interference with adjacent devices.

Figure 13:
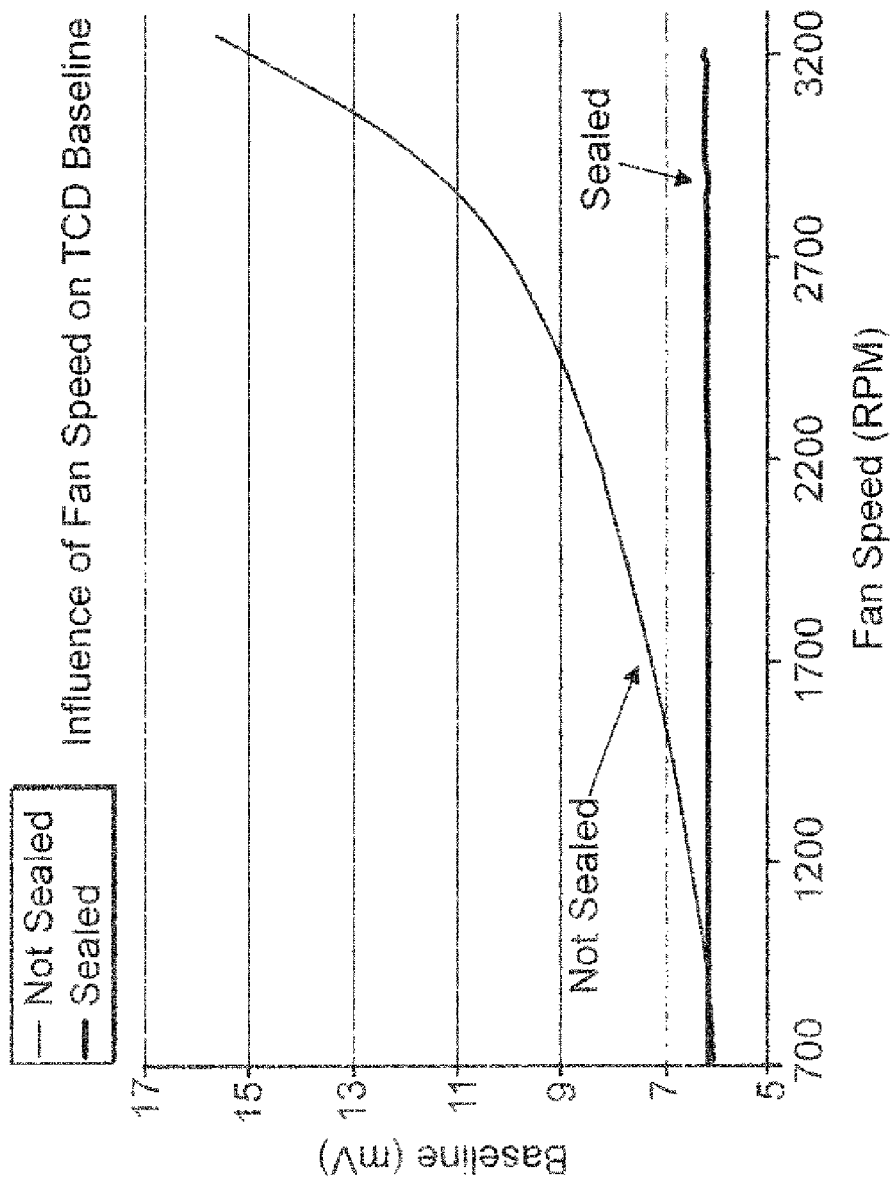
FIG. 13 is graph showing the effect of fan speed on a detector baseline, in accordance with certain examples.

In accordance with certain examples, it may also be desirable to seal the detector of the system from the fan to avoid air drafts that may affect the detector response. For example, and referring to FIG. 13, the baseline of a thermal conductivity detector (TCD) was measured as a function of fan speed. A TCD responds to the thermal conductivity of a gas flowing past heated filaments arranged in a Wheatstone bridge configuration. As such, it is sensitive to any flow that results in a differential temperature across the bridge circuit. The TCD may be constructed using a close-tolerance housing in combination with insulation to reduce the flow of oven air around the detector, thus reducing degradation in performance due to this undesired flow. The variable speed fan design disclosed herein provides a variable gas flow around the TCD housing in response to changes in fan speed. This variation in flow results in a dramatic baseline shift that may compromise chromatographic performance (see 'not sealed' baseline in FIG. 13). As conventional ovens only have a single fan speed, the TCD response due to oven gas flow variation is generally unnoticed. Hermetic sealing of the flow channel path, using a high-temperature bonding material (e.g., Aremco PYRO-PUTTY 950) may block the flow path and prevent TCD baseline shift (see green 'Sealed' baseline in FIG. 13). This hermetic sealing of the flow channels will also prevent any noise degradation in TCD performance that would result from any variations in fan speed (e.g., fan speed instability as a result of voltage fluctuations).

Figure 14:
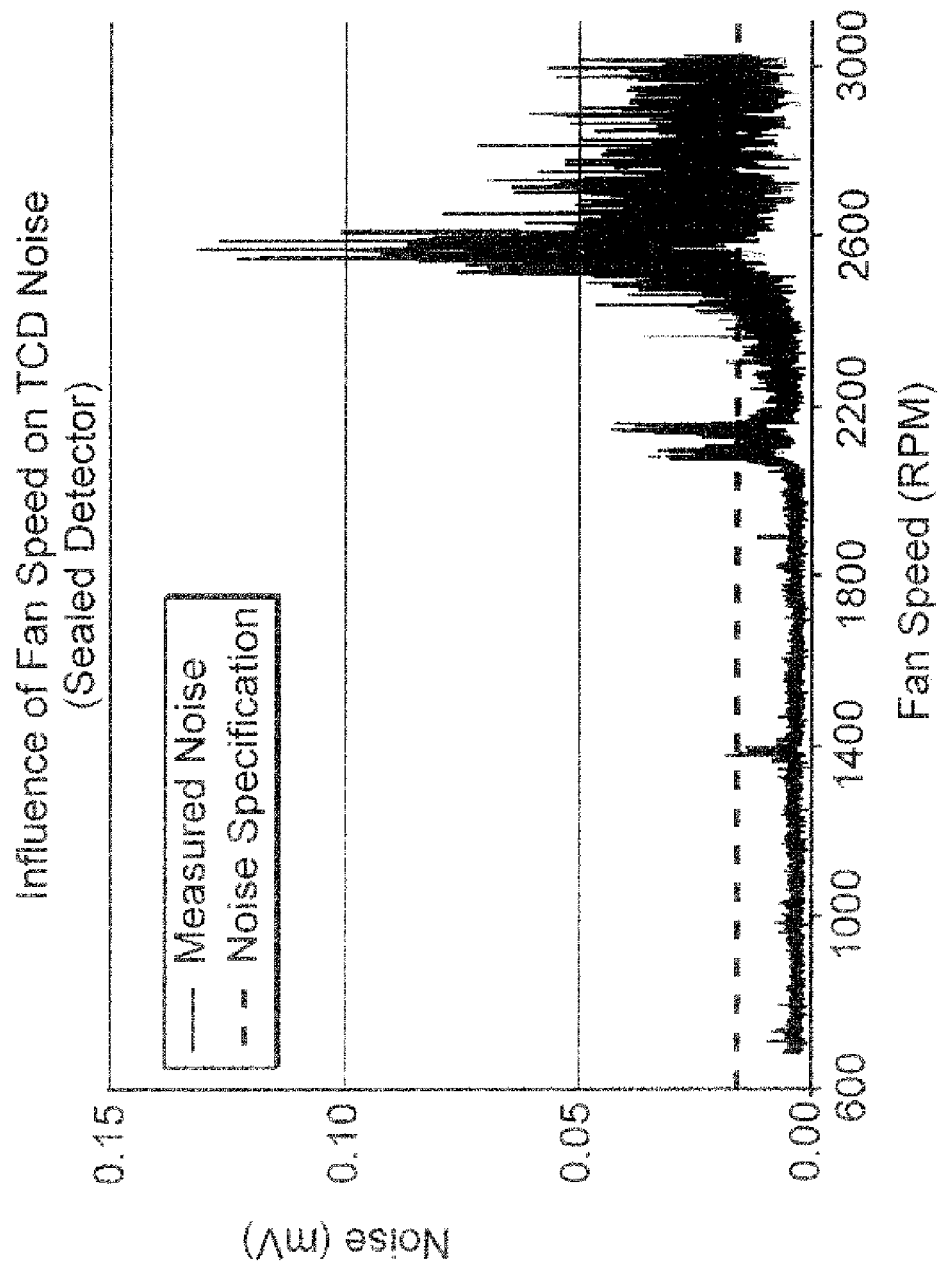
FIG. 14 is a graph showing the vibrational noise generated by a fan at different fan speeds, in accordance with certain examples.

In accordance with certain examples, in embodiments where the fan speed is modulated, it may be desirable to modulate the fan speed at a position where the vibrational or electrical noise does not substantially affect the detector. The TCD responds to the thermal conductivity of a gas flowing past heated filaments arranged in a Wheatstone bridge configuration. To achieve the desired high sensitivity to small changes in thermal conductivity of the gas flowing past the heated filament, fine resistance-wire filaments are used (e.g., typically 25 microns in diameter). Such fine wires can be sensitive to vibration, and in particular can be sensitive to resonance vibrations caused by harmonic pickup from a vibrational noise source. The fan used to circulate the air within the oven is a potential source of vibration. The fan in many ovens operates at a fixed frequency of 1400 rpm. By measuring the TCD noise as the fan speed is changed, the noise profile of the TCD may be determined and used to avoid those fan speed regions where the TCD is sensitive to resonance vibrations. An example of this fan speed scan is shown in FIG. 14, where the measured noise is compared to the noise specification for the detector. For this particular TCD, operating at 1370-1390 RPM would provide decreased performance than operation at 1400-1410 RPM due to the increased vibrational noise around 1370-1390 rpm. The default fan speed (e.g., nominally 1400 RPM) can be adjusted, for example, by a trimpot to provide improved TCD noise performance.

In accordance with certain examples, the ovens disclosed herein that include a recirculation path, fan modulation and/or air intake and air exhaust aperture adjustment may be used in a chromatography system. The exact nature of the chromatography system selected may vary and in certain examples, the chromatography system is a gas chromatography system, a liquid chromatography system, or a supercritical fluid chromatography system. When used in a liquid chromatography system, the oven may provide for a fixed or variable temperature to the column that is below the vaporization temperature of the solvents being used. Similarly, when used in supercritical fluid chromatography, the oven may be used to provide precise temperature control of the mobile phase. When used in a gas chromatography system, the oven may be used to provide a constant temperature or a temperature ramp. Examples of each of these chromatography systems are described in more detail below.

Figure 15:
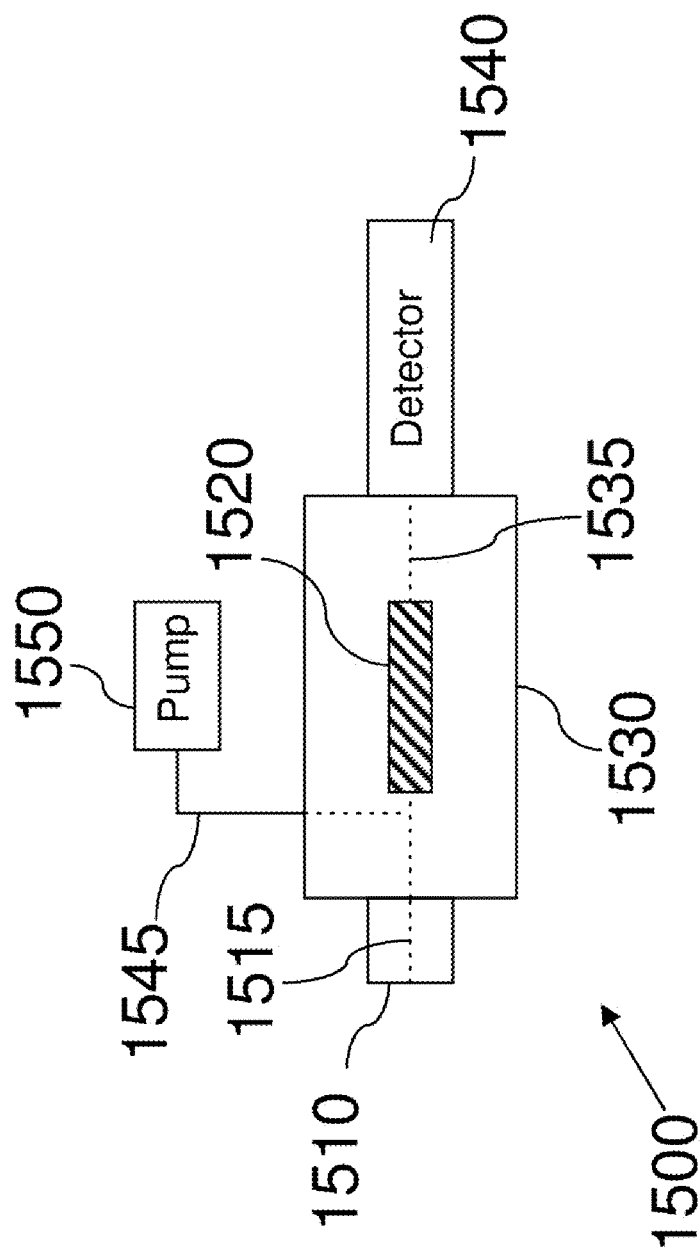
FIG. 15 is a schematic of a liquid chromatography system, in accordance with certain examples.

In accordance with certain examples, a liquid chromatography system comprising an oven, which may be any of the illustrative ovens disclosed herein, e.g., an oven including one or more of a recirculation path, fan modulation and/or air intake and air exhaust aperture modulation is provided. The liquid chromatography system may be a high performance liquid chromatography (HPLC) system, a fast performance liquid chromatography (FPLC) system or other suitable liquid chromatography systems. An example of an HPLC system is shown in FIG. 15. The HPLC system comprises a sample introduction device 1510, such as a sample loop injector that is fluidically coupled to a chromatography column 1520 through a fluid flow path 1515. The column 1520 is positioned in an oven 1530. Embodiments of the oven disclosed herein may provide a temperature that is substantially the same in the space occupied by the column such that different regions of the column are not at different temperatures. The column 1520 is also fluidically coupled to a detector 1540 through a fluid flow path 1535. One or more pumps, such as pump 1550, may be fluidically coupled to the column 1520 through a flow path 1545 to provide mobile phase to the column 1520 for separating species introduced into the system 1500 through the sample introduction device 1510.

In the HPLC system shown in FIG. 15, existing column and column materials may be used, e.g., pellicular and porous particles may be used to produce stationary phases. Suitable commercially available HPLC columns, such as PerkinElmer Brownlee™ columns, may be obtained, for example, from PerkinElmer, Inc. (Waltham, Mass.). Existing detectors, such as absorbance detectors, fluorescence detectors, infrared detectors, light scattering detectors, optical activity detectors, electrochemical detectors, refractive index detectors, conductivity detectors, mass spectrometers, element selective detectors, photoionization detectors or other suitable detectors may be used to detect species eluting from the column. The HPLC system 1500 is typically controlled with a controller that implements one or more algorithms to separate species injected into the column. Suitable analysis software may also be included with the system to quantify eluent peaks. It will be within the ability of the person of ordinary skill in the art, given the benefit of this disclosure, to include other suitable features in an HPLC system.

Figure 16:
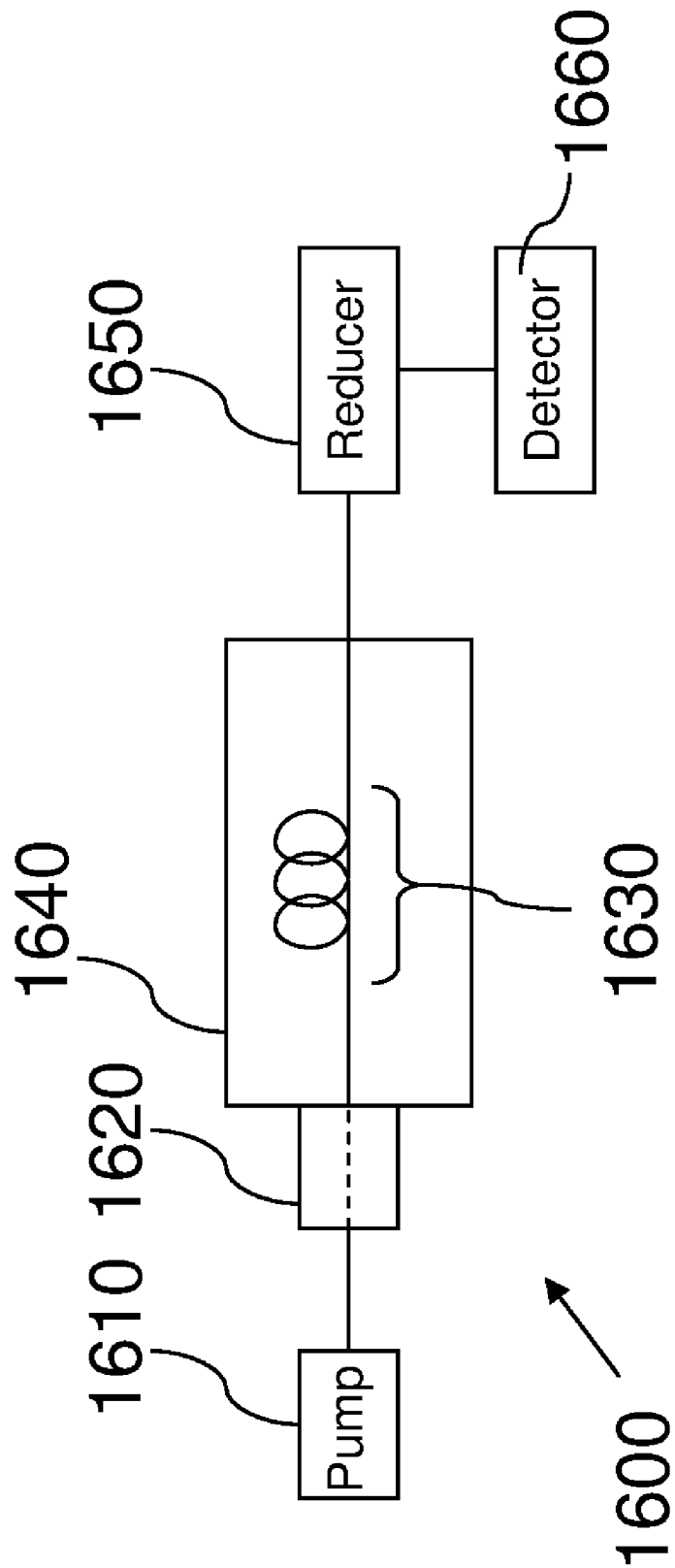
FIG. 16 is a schematic of a supercritical fluid chromatography system, in accordance with certain examples.

In accordance with certain examples, a supercritical fluid chromatography (SFC) system comprising an oven is provided. Referring to FIG. 16, the SFC system 1600 includes a pump 1610 fluidically coupled to a sample introduction device 1620. The sample introduction device is fluidically coupled to a column 1630 in an oven 1640, which may include one or more of a recirculation path, fan modulation and/or air intake and air exhaust aperture adjustment. The oven 1620 provides precise control of the mobile phase and due to the substantially constant temperature in different regions of the oven, the oven assists in maintaining a desired temperature, e.g., a temperature above, below or at the critical temperature of a substance. Embodiments of the oven disclosed herein may provide a temperature that is substantially the same in the space occupied by the column such that different regions of the column are not at different temperatures. The column 1630 may be fluidically coupled to a restrictor 1650 to increase pressure in the system 1600 and convert the supercritical fluid to a gas for detection by detector 1660. Alternatively, the column 1630 may itself be restricted at one end to convert the supercritical fluid into a gas and the restrictor may be omitted. Detectors similar to those discussed below in reference to gas chromatography are typically used to detect the species. The system is typically controlled with a controller to control the pressure/density in the system as well as to control flow rates, oven temperature, and the like.

Figure 17:
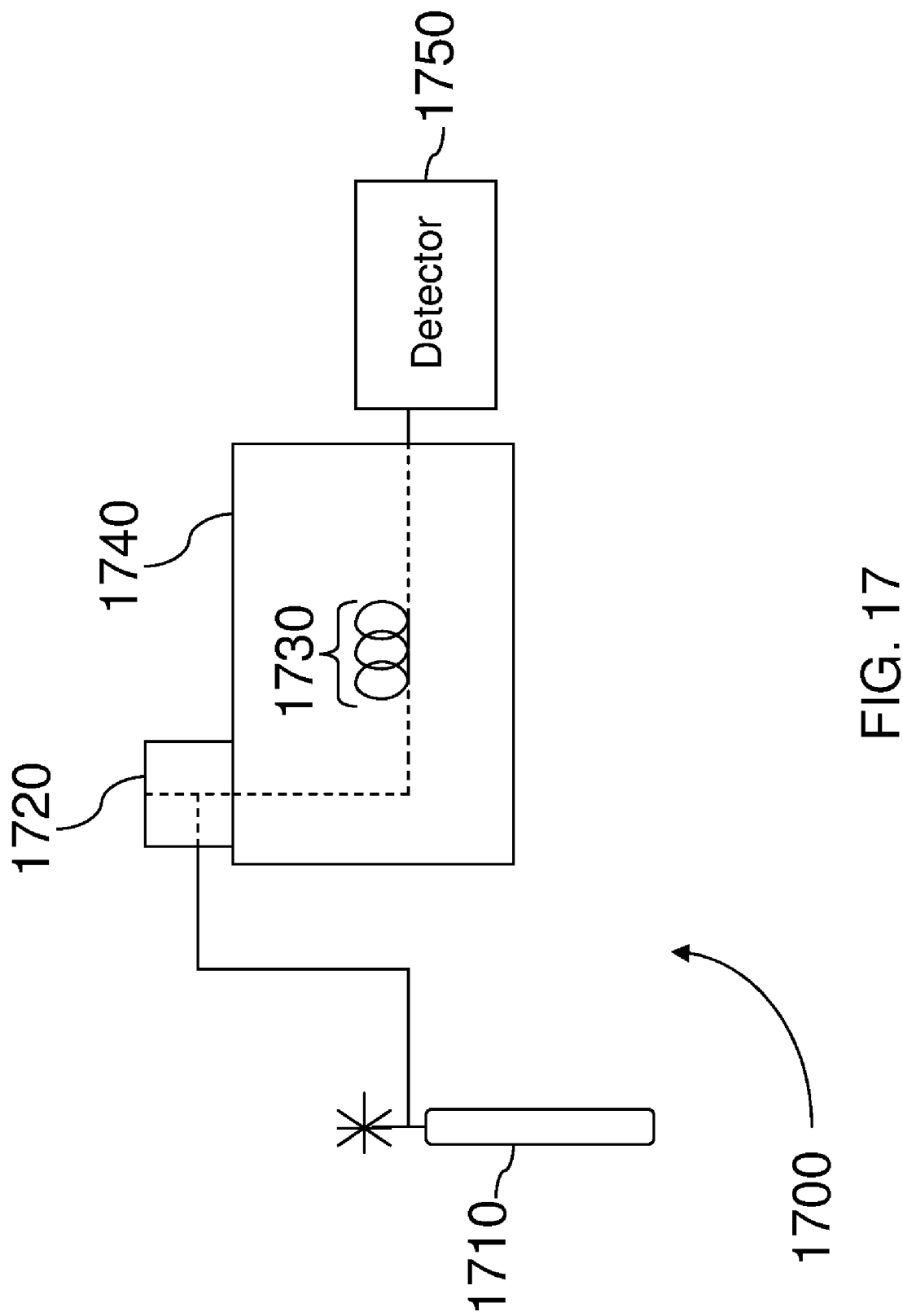
FIG. 17 is a schematic of a gas chromatography system, in accordance with certain examples.

In accordance with certain examples, a gas chromatography system comprising an oven disclosed herein, e.g., an oven with one or more of a recirculation path, fan modulation and/or air intake and air exhaust aperture adjustment is provided. Referring to FIG. 17, a gas chromatography system 1700 includes a carrier gas source 1710 fluidically coupled to a sample introduction device 1720. The carrier gas is typically helium, nitrogen, argon, carbon dioxide or hydrogen though other gases may also be used. The sample introduction device 1720 may be fluidically coupled to a column 1730, which contains a stationary phase, in an oven 1740. Species are separated by the column 1730 and are detected by a detector 1750, which is fluidically coupled to the column 1730. Embodiments of the oven disclosed herein may provide a temperature that is substantially the same in the space occupied by the column such that different regions of the column are at substantially the same temperature.

In accordance with certain examples, the sample introduction devices of the chromatography systems disclosed herein may be used to manually load sample into the system or may be used to provide automated loading of sample in the system. In certain embodiments, the sample introduction device includes an injector configured to receive sample through a syringe or a needle. A portion of the injected sample, or the entire sample depending on the injection volume, may pass to the chromatography column for separation. The remainder of the sample may be passed to waste. Embodiments of the oven disclosed herein that provide a consistent cool down time are particularly suited for use with autosamplers due to the consistent cool down times provided by the ovens. It will be recognized by the person of ordinary skill in the art, given the benefit of this disclosure, that the exact type of sample introduction device may depend, at least in part, on the type of column e.g., capillary vs. non-capillary column. In a typical sample introduction device for use with a packed column in a gas chromatography system, a small amount of liquid, e.g., a few microliters, may be injected through a silicon rubber septum into a hot GC injector that may be lined with an inert glass tube. The injector may be heated using a metal heater block that is thermostatically controlled. The hot GC injector vaporizes the sample, and a pressurized, inert, carrier gas—which is continually flowing from a gas regulator through the injector and into the GC column, sweeps the gaseous sample, solvent, analyte and all, onto the column. In the packed column injector, substantially all of the vaporized sample enters onto the column. In another sample introduction device for use with a capillary column, a split line or vent may be present such that only a portion of the injected sample is passed to the column. By including a split line on the injector, it may be possible to achieve better precision in multiple injections.

The ovens disclosed herein may be used with many different types of gas chromatography columns including conventional packed columns and capillary columns. Conventional packed columns are those where a chromatography medium has been packed into the bore of a column. Capillary columns have more theoretical plates per meter as compared to packed columns. Thus it may be possible to achieve better separation using a capillary column than a packed column having the same length as the capillary column. Suitable commercially available conventional and capillary columns are available from PerkinElmer, Inc. (Waltham, Mass.).

In certain examples, the detector of the GC system is generally designed to respond or to measure very small quantities of sample vapor contained in the carrier gas. As gas chromatography systems may be designed to operate over wide temperature range, e.g., ambient temperature to about 450° C., the detector should be able to operate within this temperature range to avoid solute condensation within the detector. The detector may be a bulk property detector or a solute property detector. Bulk property detectors measure or detect a bulk physical property of the bulk eluent, e.g., conductivity, dielectric constant, refractive index, etc. Solute property detectors measure or detect a physical or chemical property unique to the eluent, e.g., fluorescence, phosphorescence, heat of combustion, etc. In certain examples, the detector may be a mass spectrometer, as discussed further below.

In some examples, the detector may be an ionization detector. A particularly useful ionization detector is a flame ionization detector. Flame ionization detectors (FID) have a wide operating range and can generally detect all substances that include a least one carbon atom. In a flame ionization detector, hydrogen is usually mixed with the column eluent and burned at a small jet. Surrounding the flame is a generally cylindrical electrode. A voltage may be applied between the jet and the electrode to collect the ions that are formed in the flame. The resulting current may be amplified by a high impedance amplifier, and the output may be provided to a data acquisition system, a potentiometric recorder or other suitable output devices. The detector usually operates with three separate gas supplies together with flow regulators. The gases normally used are hydrogen for combustion, helium or nitrogen for the carrier gas and oxygen or air as the combustion agent. The detector may be temperature controlled in a separate oven or in the same oven that contains the chromatography column. Temperature control of the detector is typically performed to reduce the likelihood that solutes condense in the connecting tubing.

In some examples, the detector may be a hot wire detector. In some examples, a hot wire detector may be constructed using two heated filaments positioned in the arms of a Wheatstone bridge. One filament is suspended in the eluent gas from the column, and the other filament is in a reference stream of gas. As a solute elutes from the column, both the thermal conductivity and the heat capacity of the gas change. This change alters the heat loss and, thus, the temperature of the filament, which in turn changes its resistance. The bridge is unbalanced and the out-of-balance signal is passed to a suitable monitoring device. This detector generally responds to all solutes that differ in heat capacity and thermal conductivity from those of the carrier gas. In some examples, the hot wire detector may be configured as a thermal conductivity detector.

In certain examples, the detector may be a nitrogen phosphorous detector (NPD). An NPD has a similar construction to that of an FID but operates using different principles. In one embodiment of a NPD, a rubidium or cesium chloride bead is contained inside a heater coil situated close to a hydrogen jet. The bead is positioned above the jet and heated by a coil, over which the carrier gas from the GC is mixed with hydrogen. If it is desirable for the detector to respond to both nitrogen and phosphorus, then the hydrogen flow may be reduced so that the gas does not ignite at the jet. If the detector is to respond to phosphorus only, a large flow of hydrogen may be used to burn the mixture at the jet. The heated alkali bead emits electrons (by thermionic emission) that are then collected at the anode. When a solute that contains nitrogen or phosphorus elutes from the column, the partially combusted nitrogen and phosphorus materials may be adsorbed on the surface of the bead. The adsorbed material reduces the work function of bead and permits greater thermionic emission and an increase in the measured current.

In additional examples, the detector may be a photometric detector, which is also referred to as an emissivity detector. In one embodiment of a photometric detector, hydrogen is mixed with column eluent and is burned in a flame jet. The jet and the actual flame may be shielded to prevent light from the flame reaching a photomultiplier or other light detector. The base of the jet may be heated to prevent vapor condensation. The light emitted above the flame may pass to a wavelength selector filter and on to a photomultiplier for detection.

Figure 18:
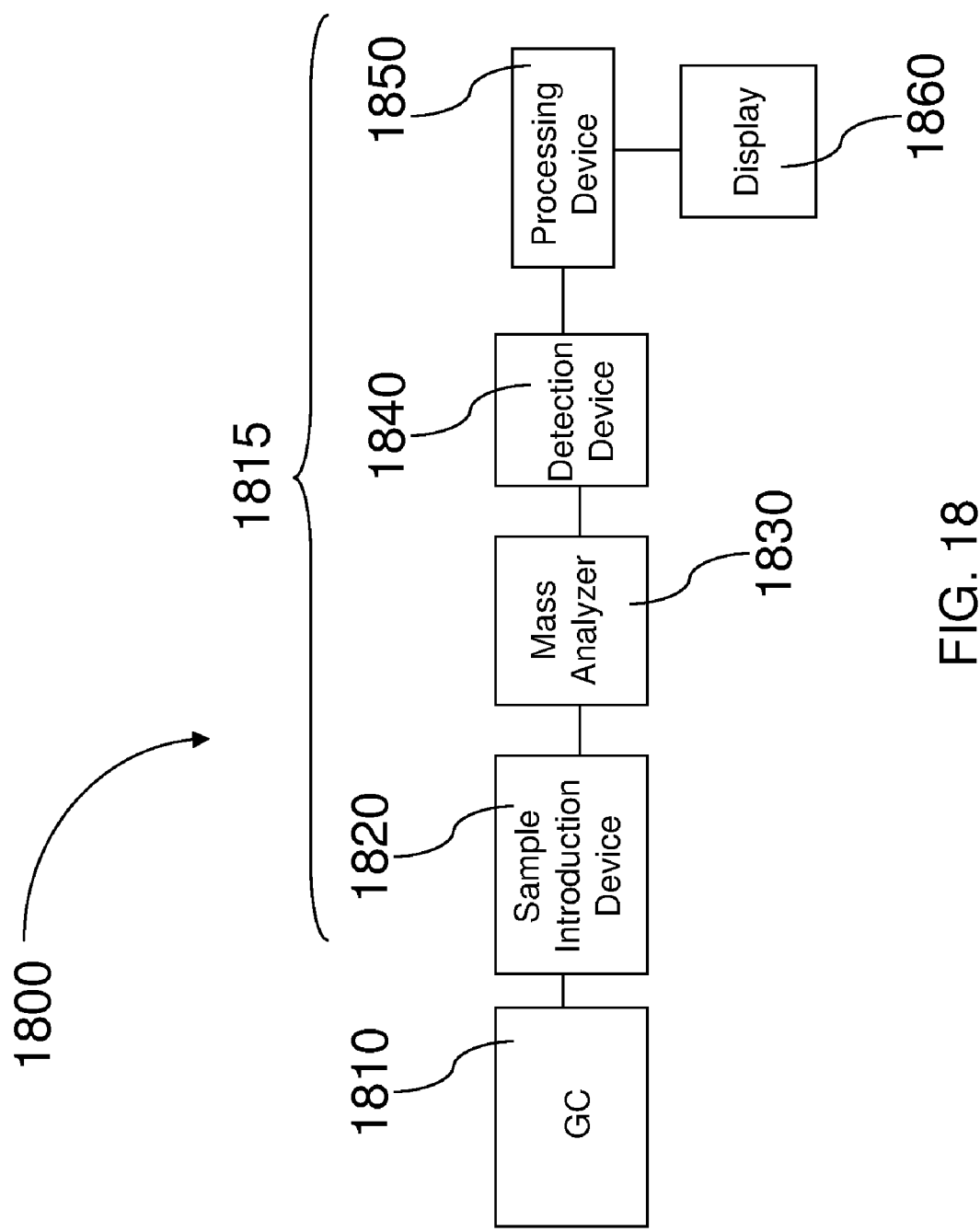
FIG. 18 is a schematic of a gas chromatography-mass spectrometer system, in accordance with certain examples.

In accordance with certain examples, the gas chromatography device may be coupled to, e.g., hyphenated with, one or more other analytical techniques. For example, the gas chromatography system may be coupled to a mass spectrometer to provide a GC-MS. An illustration of a GC-MS is shown in FIG. 18. The GC-MS system 1800 includes a GC 1810 fluidically coupled to a MS device 1815 that includes a sample introduction device 1820, a mass analyzer 1830, a detection device 1840, a processing device 1850 and a display 1860. The sample introduction device 1820, the mass analyzer 1830 and the detection device 1840 may be operated at reduced pressures using one or more vacuum pumps, such as a turbomolecular pump, an oil diffusion pump or the like. In certain examples, however, only the mass analyzer 1830 and the detection device 1840 may be operated at reduced pressures. The sample introduction device 1820 may include an inlet system configured to receive eluent from the GC 1810 and to the mass analyzer 1830. The inlet system may include one or more batch inlets, direct probe inlets and/or chromatographic inlets. The sample introduction device 1820 may be an injector, a nebulizer or other suitable devices that may provide gaseous samples to the mass analyzer 1830. The mass analyzer 1830 may take numerous forms depending generally on the sample nature, desired resolution, etc. and exemplary mass analyzers are discussed further below. The detection device 1840 may be any suitable detection device that may be used with existing mass spectrometers, e.g., electron multipliers, photomultipliers, Faraday cups, coated photographic plates, ion traps, scintillation detectors, etc., and other suitable devices that will be selected by the person of ordinary skill in the art, given the benefit of this disclosure. The processing device 1850 typically includes a microprocessor and/or computer and suitable software for analysis of samples introduced into GC-MS device 1800. One or more databases may be accessed by the processing device 1850 for determination of the chemical identity of species introduced into GC-MS device 1800. Other suitable additional devices known in the art may also be used with the GC-MS device 1800 including, but not limited to autosamplers commercially available from PerkinElmer, Inc., e.g., those supplied for use in or with a Clarus® 600 instrument. The autosamplers may be integrated into the device or may be separate and coupled to the device.

In accordance with certain examples, the mass analyzer of GC-MS device 1800 may take numerous forms depending on the desired resolution and the nature of the introduced sample. In certain examples, the mass analyzer is a scanning mass analyzer, a magnetic sector analyzer (e.g., for use in single and double-focusing MS devices), a quadrupole mass analyzer, an ion trap analyzer (e.g., cyclotrons, quadrupole ions traps), time-of-flight analyzers (e.g., matrix-assisted laser desorbed ionization time of flight analyzers), and other suitable mass analyzers that may separate species with different mass-to-charge ratios.

In accordance with certain other examples, a device that implements one or more ionization methods commonly used in mass spectroscopy may also be included in the MS device 1800. For example, electron impact sources may be assembled to ionize species prior to entry of ions into the mass analyzer. In other examples, chemical ionization sources may be used to ionize species prior to entry of ions into the mass analyzer. In yet other examples, field ionization sources may be used to ionize species prior to entry of ions into the mass analyzer. In still other examples, desorption sources such as, for example, those sources configured for fast atom bombardment, field desorption, laser desorption, plasma desorption, thermal desorption, electrohydrodynamic ionization/desorption, etc. may be used. In yet other examples, thermospray ionization sources may be used. It will be within the ability of the person of ordinary skill in the art, given the benefit of this disclosure, to select suitable devices for ionization for use with the devices disclosed herein.

In accordance with certain examples, other non-MS analytical techniques may be coupled to the GC. For example, systems may include two or more GC's coupled to each other with or without intervening devices or systems. In some examples, the GC may be coupled to an optical device such as, for example, an infrared spectrometer. In yet other examples, the GC may be coupled to a nuclear magnetic resonance, electron spin resonance, electrochemical or other device. In certain examples, the GC may be coupled downstream of a liquid chromatograph to receive liquid eluent from the liquid chromatograph. Additional devices that may be coupled to a GC will be readily selected by the person of ordinary skill in the art, given the benefit of this disclosure.

Figure 19:
FIG. 19 is a graph showing a temperature ramp, in accordance with certain examples.

In accordance with certain examples, the ovens disclosed herein may be used to provide a constant temperature during an analysis or may be used to provide a temperature ramp. In embodiments where the oven provides a temperature ramp, the temperature may be increased step-wise from a starting temperature to one or more additional temperatures. The temperature of the oven is initially at about 50° C. Once the sample is injected, the temperature may be increased linearly to 70° C. at a suitable rate of, for example, about 140° C./minute. The temperature may be increased again to a third temperature, e.g., 115° C., at a suitable rate of, for example, about 105° C./minute. The temperature may be further increased to a fourth temperature, e.g., about 175° C., at a suitable rate of, for example 85° C./minute. The temperature may be increased further to a fifth temperature, e.g., about 300° C., at a suitable rate of, for example, 55° C./minute. The temperature may be increased to a sixth temperature, e.g., about 450° C., at a suitable rate of, for example, 35° C./minute. Embodiments of the ovens disclosed herein may be able to cool the oven to the initial temperature, e.g., 50° C. from the highest run temperature, e.g., 450° C., in less than five minutes, more particularly in less than three minutes, e.g., two minutes or less. An illustration of this temperature ramp is shown in FIG. 19. Thus, injection-to-injection time may be reduced by such rapid cooling. Also, cool down time may be decreases by at least 50-75% as compared to operating the system with the fan at the first speed in both the analysis and cool down stages.

Figure 20:
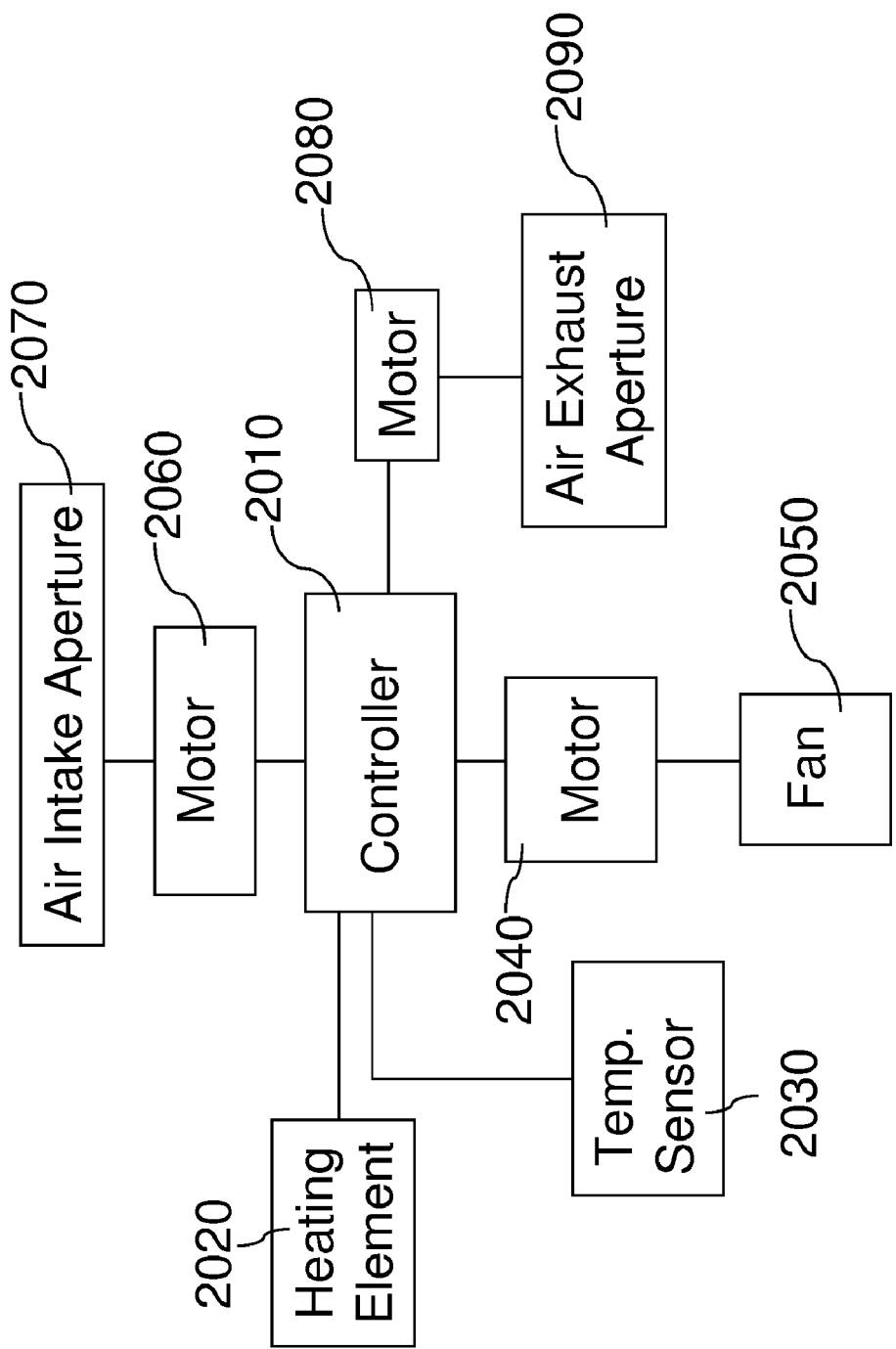
FIG. 20 is schematic of a controller coupled to various components of an oven, in accordance with certain examples.

In accordance with certain examples, the ovens and devices using them may include a controller that is programmable to receive a signal from a temperature sensor and send a signal to change the temperature, if desired, to actuate a motor to open or close an air intake aperture or an air exhaust aperture, or to modulate the fan speed. An illustration of a controller is shown in FIG. 20. The controller 2010 is coupled to a heating element 2020 to control the temperature and the rate of heating. A temperature sensor 2030 may be coupled to the controller 2010 to measure the temperature in the oven. The controller 2010 may also be coupled to a motor 2040 that is coupled to a fan 2050 in the oven. The motor 2040 may be a programmable motor, such as a programmable DC motor, that can change the fan speed depending on the temperature and/or on a signal received from the controller 2010. The controller 2010 may also be coupled to a motor 2060 which itself is coupled to an air intake aperture 2070. The motor 2060 may be used to open and close the air intake aperture 2070 to control heating and/or cooling of the oven. Similarly, the controller 2010 may be coupled to a motor 2080 which itself is coupled to an air exhaust aperture 2090. The motor 2080 may be used to open and close the air exhaust aperture 2090 to control heating and/or cooling of the oven. The controller 2010 may also include, or have access to, software or algorithms to perform a chromatographic separation including, for example, temperature control, mobile phase flow rate control, oven temperature control, data analysis and the like. Additional devices that may be coupled to a controller for use with the ovens disclosed herein will be readily selected by the person of ordinary skill in the art, given the benefit of this disclosure. Illustrative suitable controllers include, but are not limited to, proportional-integral-derivative (PID) controllers, proportional only (P) controllers, proportional-integral (PI) controllers and nonlinear adaptive controllers (e.g., artificial neural networks, fuzzy logic, genetic algorithms, combined neuro-fuzzy approaches and the like).

Certain specific examples are disclosed below to illustrate further certain aspects and features of the ovens disclosed herein.

Example 1

Figure 21:
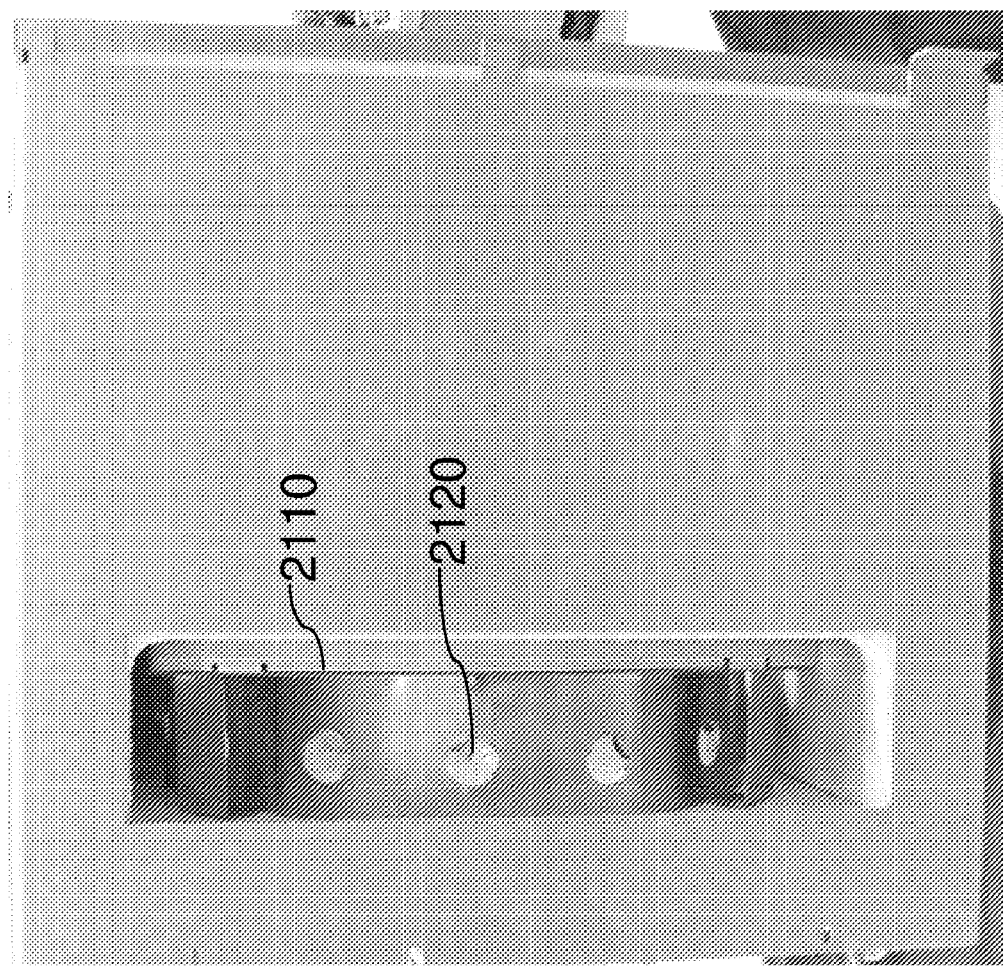
FIG. 21 is a photograph showing a side view of an oven that includes a recirculation path configured as a shroud comprising a plurality of through-holes, in accordance with certain examples.

A recirculation path that included a plurality of through-holes was produced by cutting holes in the circumference of a shroud. The holes were cut to be ¾" in diameter and there were 14 total holes equally spaced around the circumference of the shroud. The diameter of the shroud was approximately 9 inches and was made of stainless steel (0.017 inches thick). The shroud was a separate piece from the square portion of the oven and the overall assembly was riveted together in the final form. A photograph showing a side view of the shroud 2110 that includes a recirculation path comprising a plurality of through-holes, such as through-hole 2120 is shown in FIG. 21.

Example 2

A 5% w/v solution of paraffin wax in toluene was injected into the gas chromatograph with the recirculation path of Example 1. A 15 m×0.250 mm×0.1 μm 5% phenyl/dimethylpolysiloxane column was used. The flow rate of carrier gas helium was 1.0 mL/min. The starting temperature was 220° C. for 1 minute, and then the temperature was ramped to 280° C. at 2.5° C./min. Chromatograms showing the results of the separation are shown in FIGS. 22A-22C.

Figure 22A:
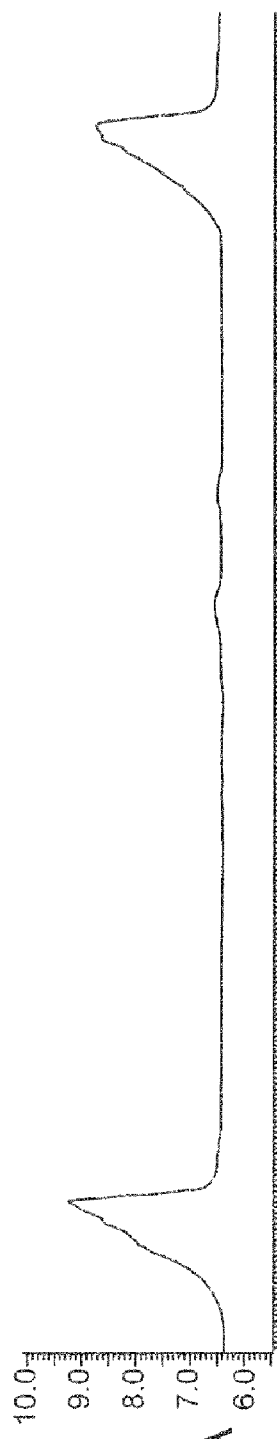
FIGS. 22A-22C are gas chromatograms run with the shroud of FIG. 21 in different positions, in accordance with certain examples.
Figure 22B:
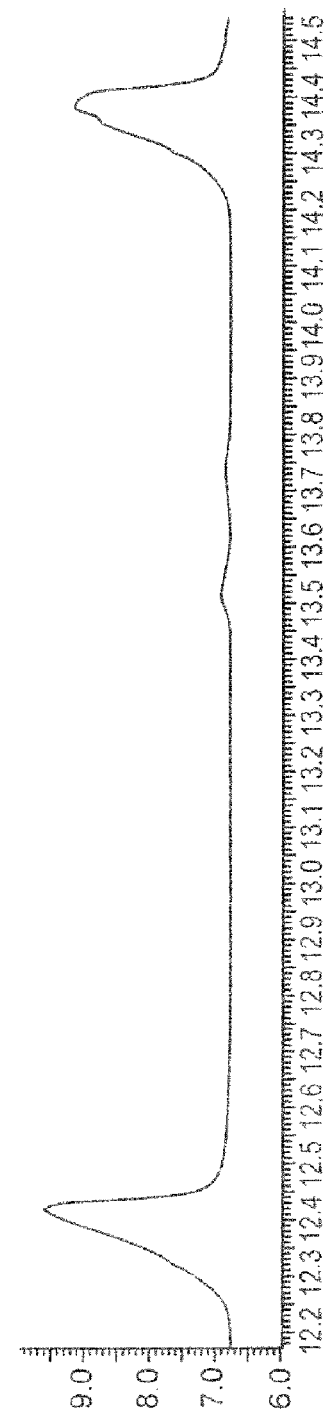
Figure 22C:
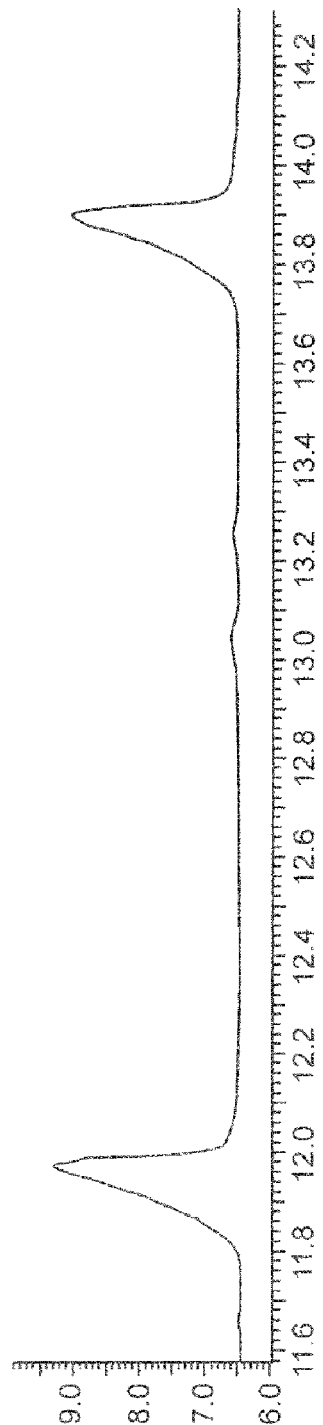

Referring to FIG. 22A, when the recirculation path was closed (the through-holes were blocked), the Christmas tree effect was evident. As the recirculation path was partially open (through-holes open about 50%), the Christmas tree effect was reduced, as shown in FIG. 22B. When the recirculation path was fully open (through-holes 100% open), the Christmas tree effect was absent, as shown in FIG. 22C.

Example 3

Figure 23A:
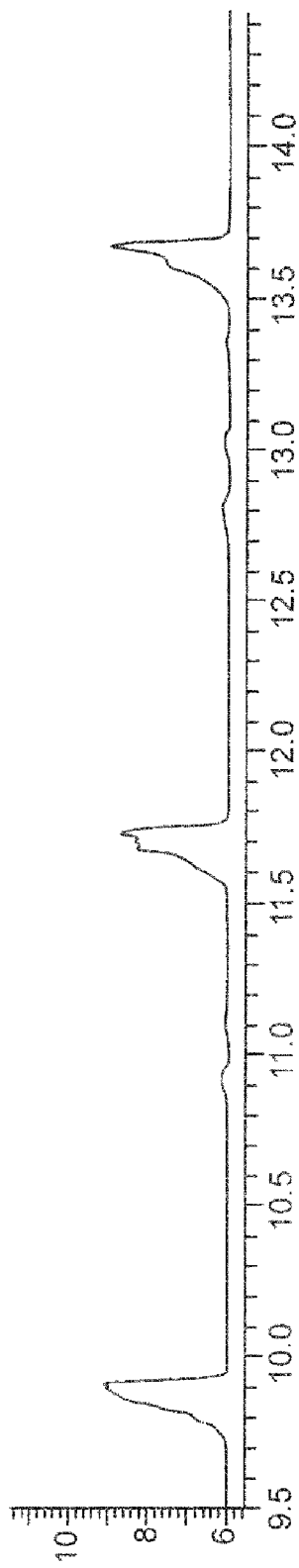
FIG. 23A is a real-time chromatogram and FIG. 23B is the processed chromatogram of FIG. 23A, in accordance with certain examples.
Figure 23B:
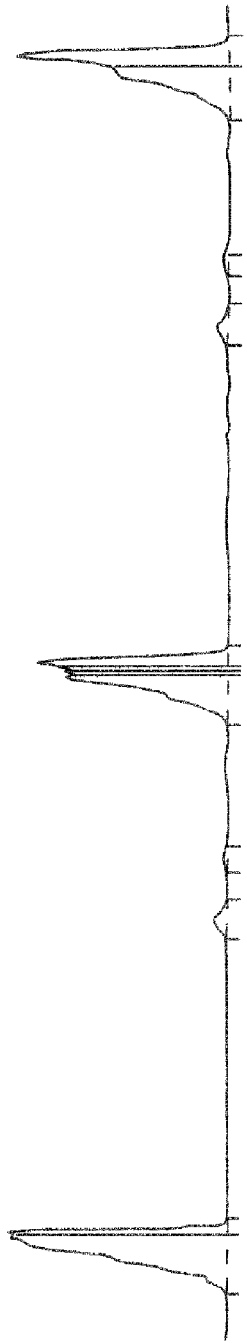

Several experiments were performed with the through-holes partially open (50% open). The conditions used were the same as those described above in Example 2 except a severe temperature gradient was induced. In one experiment, the column was placed in the line of sight of the heater. FIG. 23A shows the resulting chromatogram, and FIG. 23B shows the processed chromatogram. Because of the Christmas trees in the actual chromatogram, the instrument software identified each peak as more than one peak.

Figure 24A:
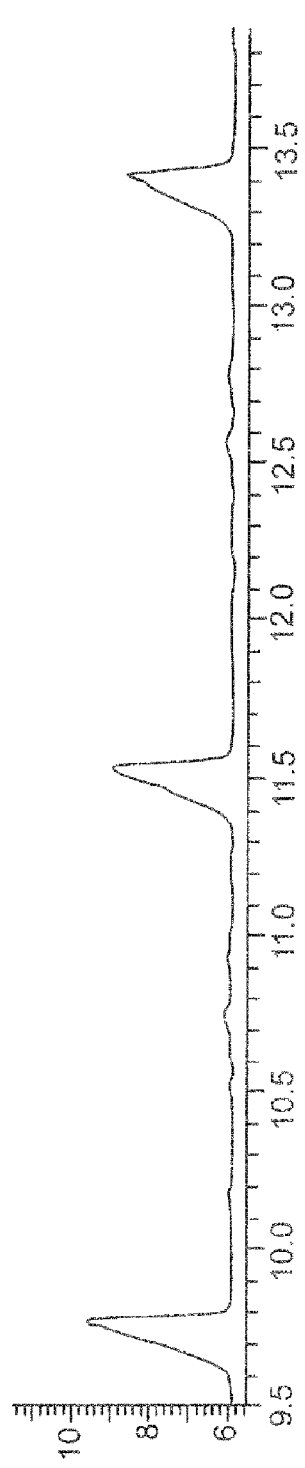
FIG. 24A is a real-time chromatogram with a column in the front position and FIG. 24B is the processed chromatogram of FIG. 24A, in accordance with certain examples.
Figure 24B:
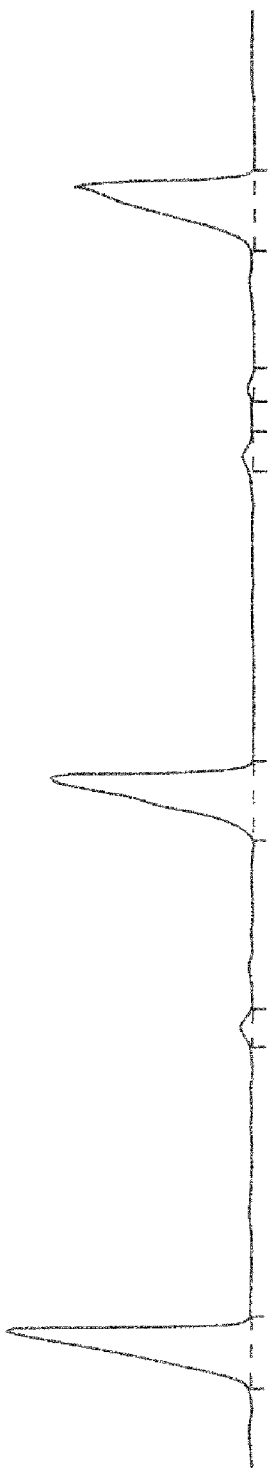

Another experiment was performed using the conditions similar to those described in Example 2, except the column was placed in the front column position (away from the heating element) and the through-holes were half open. FIG. 24A shows the resulting chromatogram, and FIG. 24B shows the processed chromatogram. Each of the relevant peaks was identified as a single peak in the processed chromatogram.

Figure 25A:
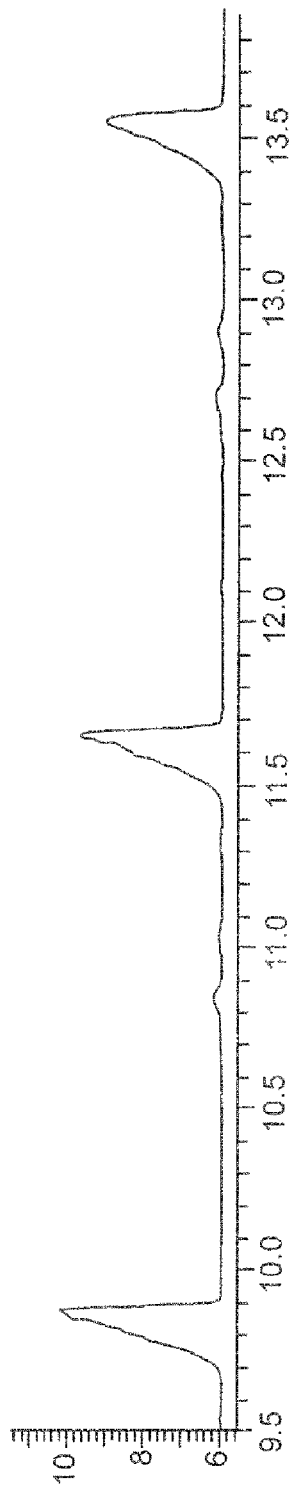
FIG. 25A is a real-time chromatogram with a column in the rear position and FIG. 25B is the processed chromatogram of FIG. 25A, in accordance with certain examples.
Figure 25B:
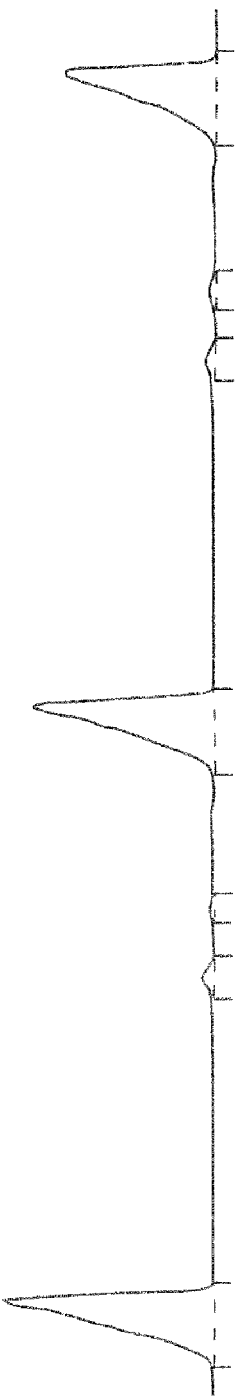

A third experiment was performed using the conditions similar to those described in Example 2, except the column was placed in the back column position (near the heating element) and the through-holes were half open. FIG. 25A shows the resulting chromatogram, and FIG. 25B shows the processed chromatogram. Each of the relevant peaks was identified as a single peak in the processed chromatogram.

Example 4

Figure 26:
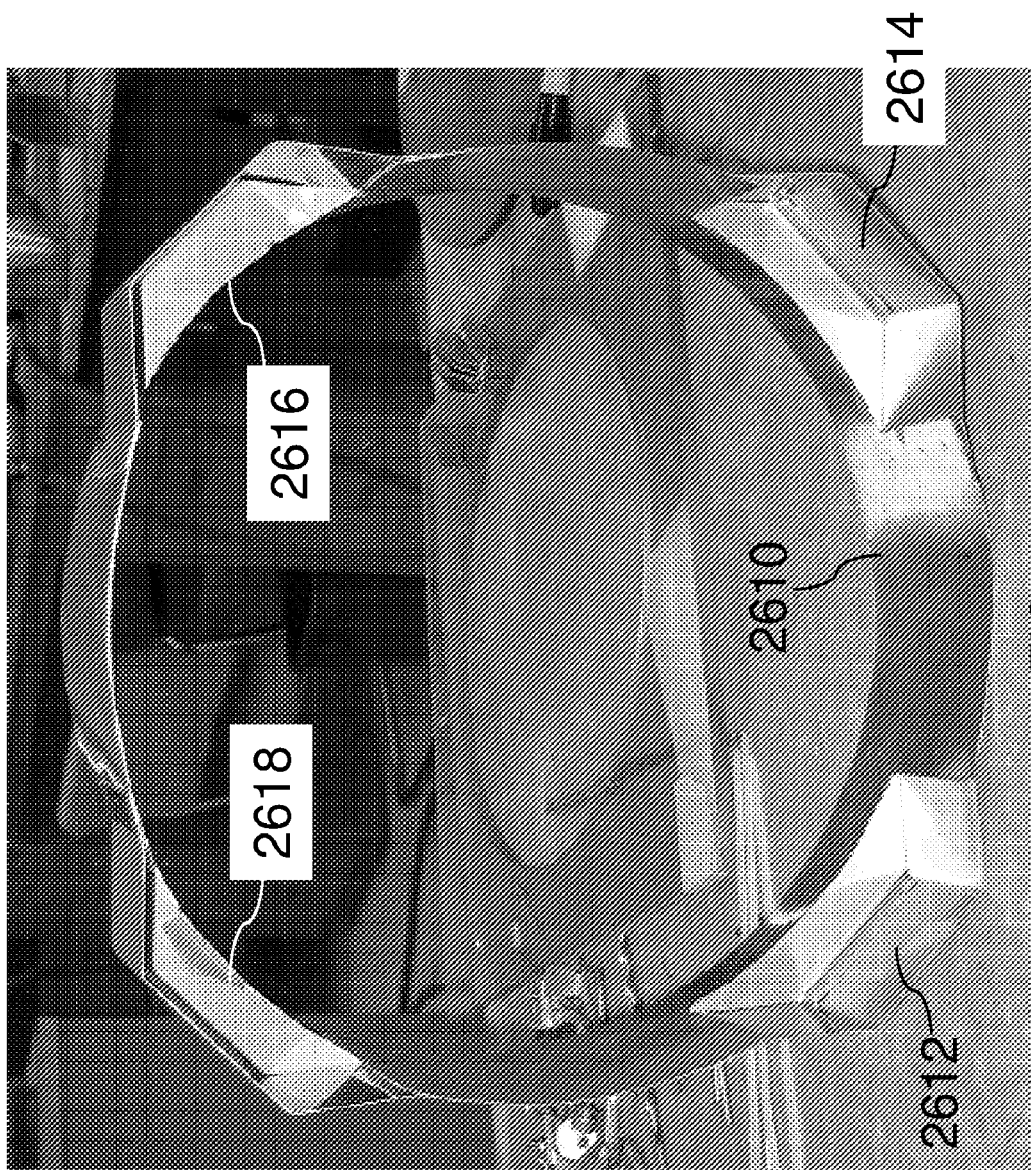
FIG. 26 is a photograph showing a side view of a recirculation path configured as an air shroud with an air scoop in each corner, in accordance with certain examples.

A recirculation path comprising an air scoop in each corner was produced using a stainless steel sheet. Referring to FIG. 26, the shroud 2610 was a stainless steel sheet (0.017 inches thick) and was rolled into a circular form. Before rolling, the part starts as a strip and four square notches were added in order to accept the scoops, 2612, 2614, 2616, and 2618. The scoops were formed from the same stainless steel material and were bent into the shape as shown in FIG. 26. The final assembly was spot welded or riveted together. A photograph showing a side view of the recirculation path 2610 including four air scoops 2612, 2614, 2616 and 2618 is shown in FIG. 26.

Figure 27:
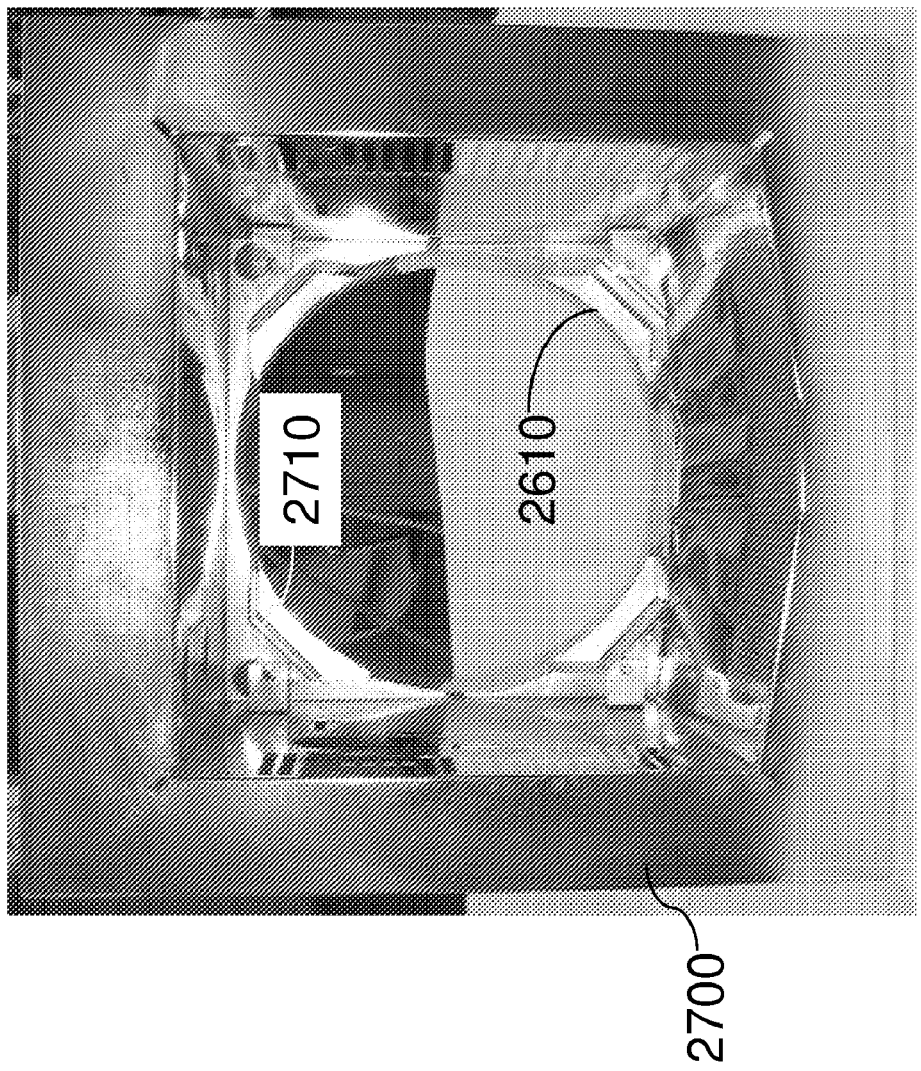
FIG. 27 is a photograph showing a side view of a recirculation path configured as an air shroud with an air scoop in each corner that has been installed into an oven housing, in accordance with certain examples.
Figure 28:
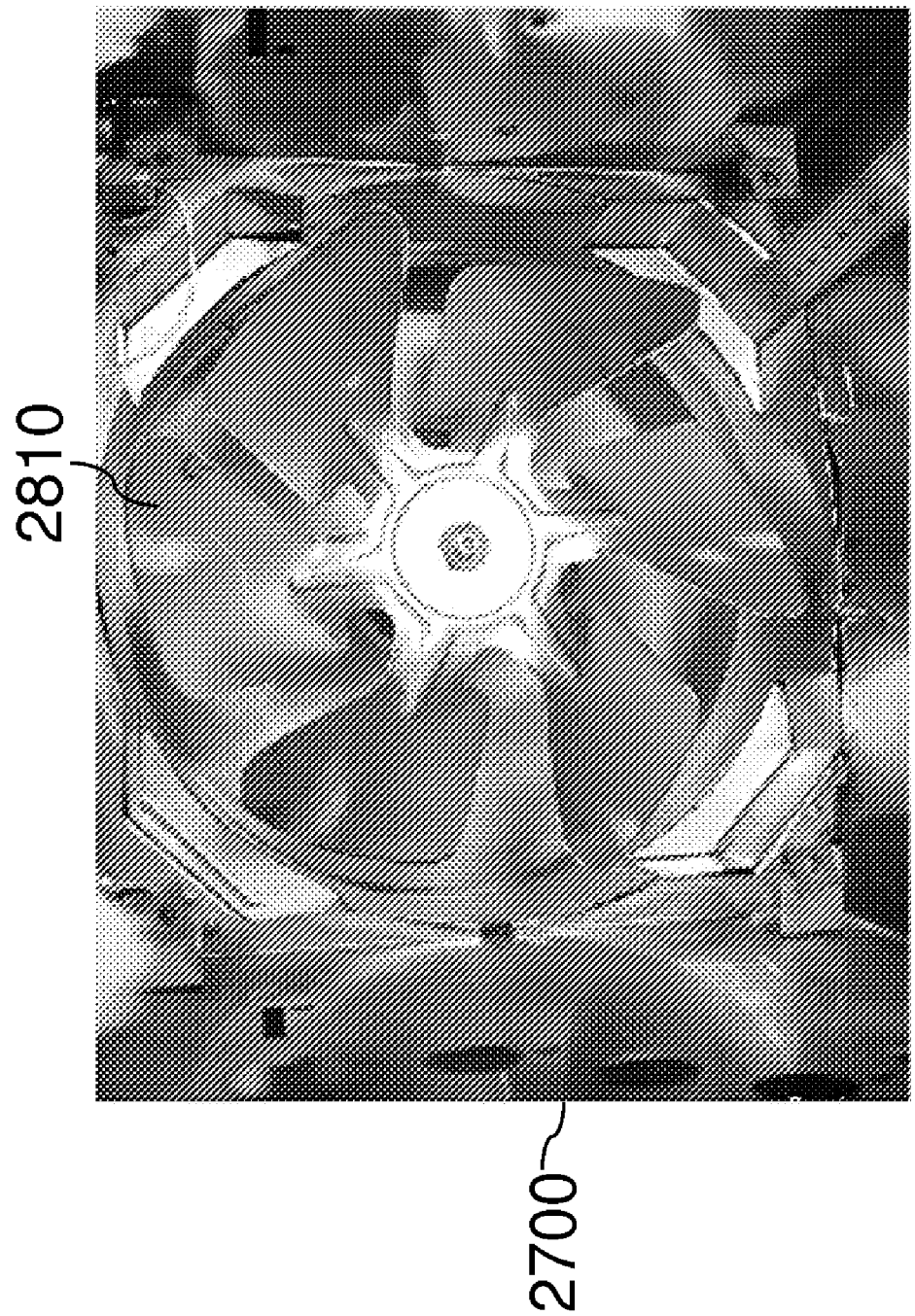
FIG. 28 is a photograph showing a fan assembly that has been installed in an oven housing, in accordance with certain examples.

The recirculation path was placed in an oven housing. A photograph showing a front view of the oven assembly 2700 is shown in FIG. 27. The recirculation path was mounted at the back of the oven assembly 2700. Tabs, such as tab 2710 were configured to receive a heating element/baffle assembly (not shown) that was used to heat the oven. The baffle assembly was present to provide a steering mechanism to move the air and prevent the column from being in a line-of-sight with the heating element. FIG. 28 is a photograph showing a fan 2810 mounted in the oven assembly 2700. The heater element (not shown) sits in front of the fan. Once the oven shell (as shown in FIG. 27) was assembled into the instrument, then the rear oven door/oven motor/fan assembly was assembled to the back of the oven. FIG. 28 is a photograph showing the result of that step.

Example 5

A Clarus® 600 gas chromatograph (commercially available from PerkinElmer, Inc.) that included the oven described above in Example 4 was used to analyze a sample. The chromatograms referenced below were obtained by injecting a 5% w/v solution of paraffin wax in toluene into the gas chromatograph with the recirculation path and having a 15 m×0.250 mm×0.1 µm 5% phenyl/dimethylpolysiloxane column. The flow rate of carrier gas helium was 1.0 mL/min. The starting temperature was 220° C. for 1 minute, and then the temperature was ramped to 280° C. at 2.5° C./min.

Figure 29A:
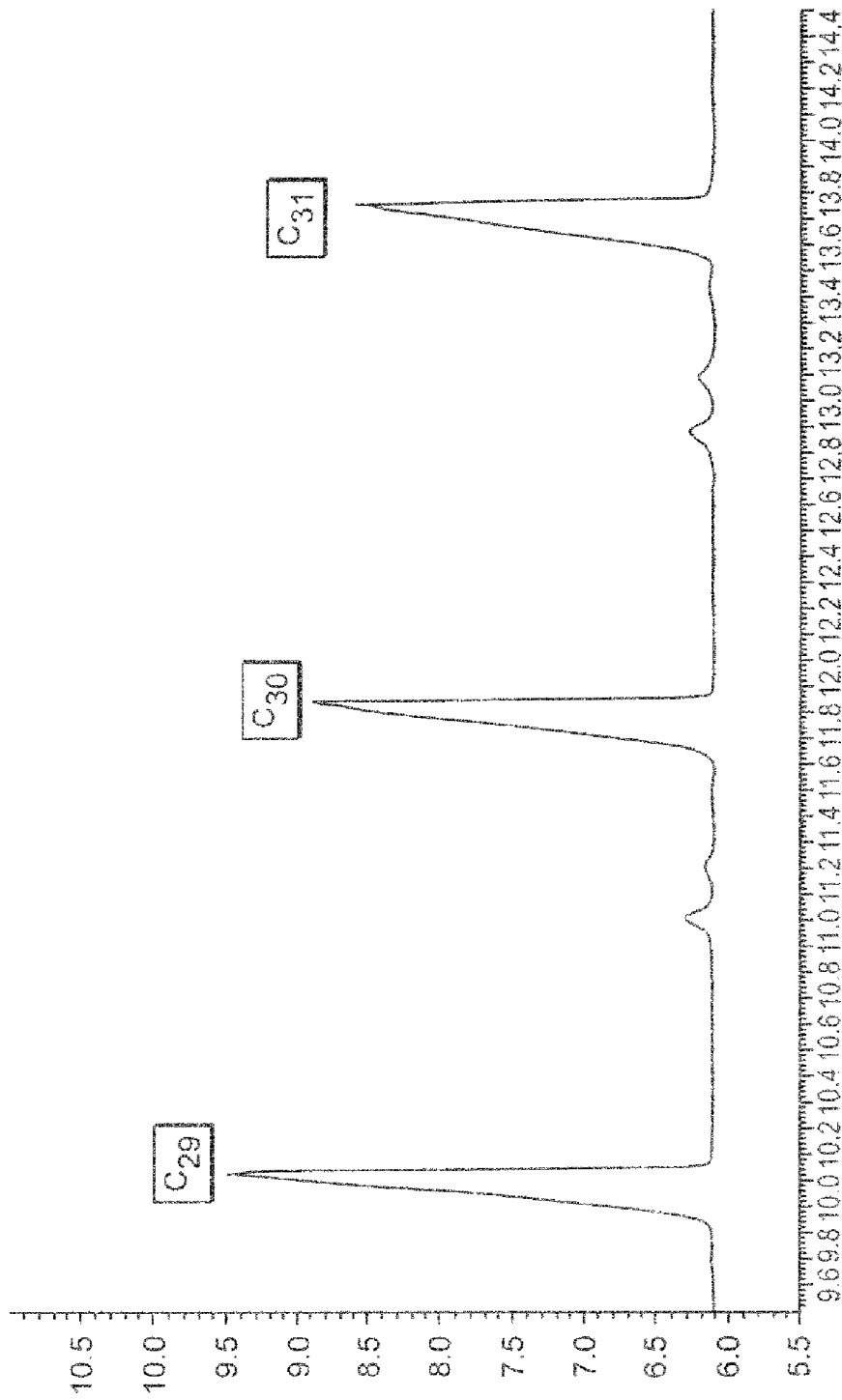
Figure 29B:
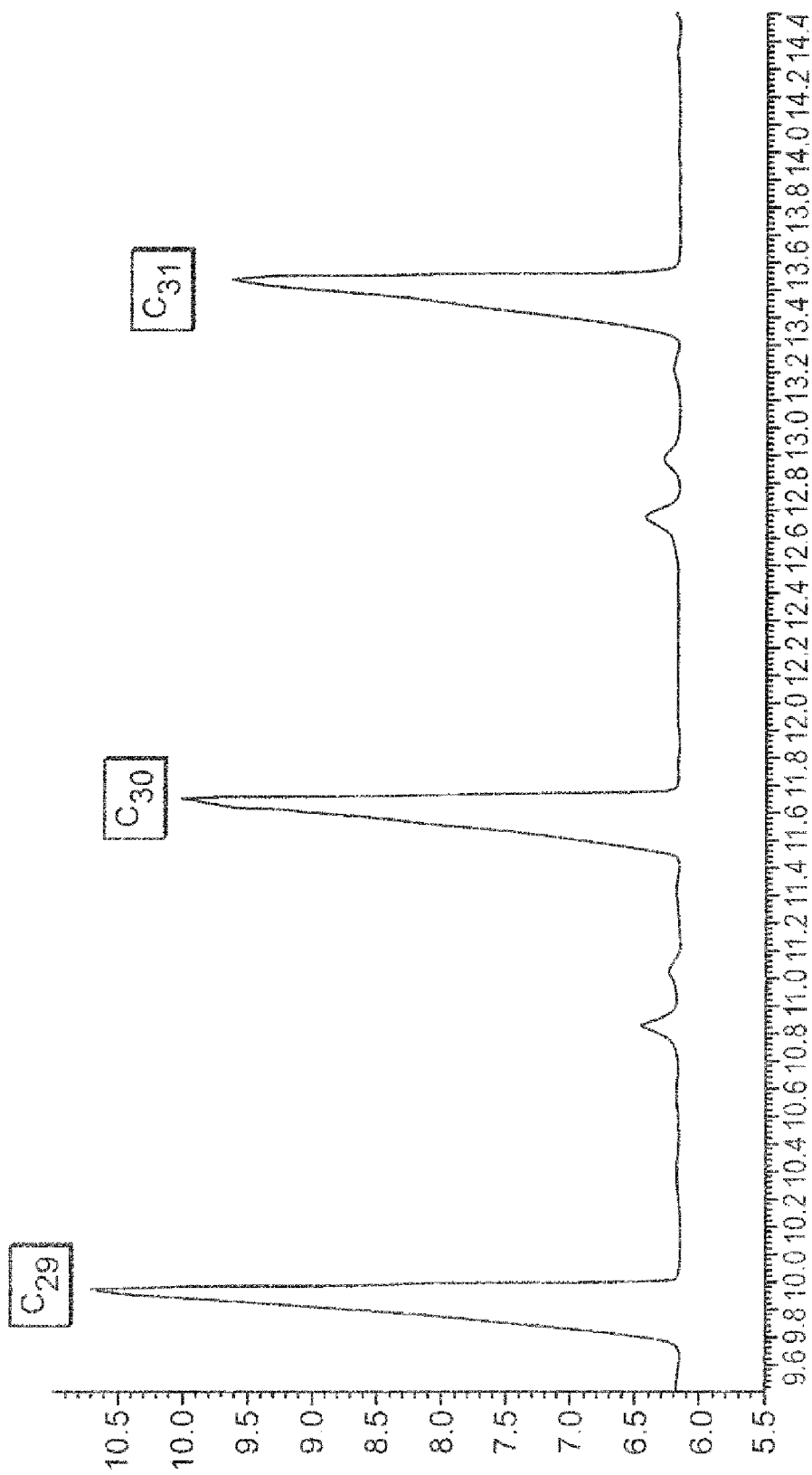

A chromatogram showing elution of the three components when the chromatography column was in the front position (away from the heater and near the air inlet aperture) is shown in FIG. 29A. A chromatogram showing elution of the three components when the chromatography column was in the back position (adjacent to the heat element) is shown in FIG. 29B. As can be seen the in FIGS. 29A and 29B, the peak shape was substantially the same indicating the temperature at the front and back positions was substantially the same.

For comparison, the same sample was run on a typical oven (with no recirculation path) under the same conditions discussed above with the column in the back position and the front position unused. A chromatogram showing the results of the separation is shown in FIG. 29C. As can be seen in FIG. 29C, Christmas trees are present resulting in poor peak shape.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples may be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A gas chromatography system comprising:
 a sample introduction device;
 a double-walled oven coupled to the sample introduction device and configured to receive a chromatography column in a space in the double-walled oven, the double-walled oven constructed and arranged to provide a substantially constant temperature to the space during an analysis stage of the gas chromatography system, the double-walled oven comprising an inner wall and an outer wall, and further configured to flow air between the inner wall and the outer wall, the double-walled oven further comprising an air intake aperture, an air exhaust aperture, and a fan configured to modulate a temperature in the oven space;
 a controller configured to adjust a degree of opening of at least one of the air intake aperture and the air exhaust aperture, and further configured to control a speed of the fan based on the degree of opening of at least one of the air intake aperture and the air exhaust aperture; and
 a detector coupled to the double-walled oven.

2. The gas chromatography system of claim 1, in which the oven comprises a recirculation path configured to circulate air to provide the substantially constant temperature to the space during the analysis stage.

3. The gas chromatography system of claim 2, in which the recirculation path includes a shroud with at least one through-hole.

4. The gas chromatography system of claim 2, in which the recirculation path includes a shroud comprising at least one air scoop.

5. The gas chromatography system of claim 2, in which the recirculation path provides a substantially constant injection-to-injection time.

6. The gas chromatography system of claim 1, wherein the degree of opening of at least one of the air intake aperture and the air exhaust aperture may be adjusted during the analysis stage of the gas chromatography system.

7. The gas chromatography system of claim 6, wherein at least one of the air intake aperture and the air exhaust aperture has a dedicated fan whose speed may be independently modulated to provide further control of the temperature within the oven space.

8. The gas chromatography system of claim 1, in which the fan may be modulated to rotate at two or more speeds during operation of the oven.

9. The gas chromatography system of claim 8, in which the fan is fluidically coupled to at least one of the air intake aperture and the air exhaust aperture.

10. The gas chromatography system of claim 8, further comprising a vent fluidically coupled to the air exhaust aperture and configured to exhaust hot air away from the space in the oven.

11. The gas chromatography system of claim 8, in which the fan is modulated at the second speed to reduce cool down time by at least 50-75% as compared to modulating the fan at the first speed.

12. The gas chromatography system of claim 8, in which the fan is modulated to rotate at a first speed of about 1400 rpm during an analysis stage and is modulated to rotate at a second speed of about 2800 rpm during a cool down stage.

13. The gas chromatography system of claim 1, in which the detector is selected from the group consisting of an ionization detector, a hot wire detector, a thermal conductivity detector, a nitrogen phosphorous detector, a photometric detector, and a mass spectrometer.

14. The gas chromatography system of claim 1, wherein the controller is configured to heat the oven space at a known rate during the analysis stage, or to cool the oven space at a known rate during a cooling stage.

15. The gas chromatography system of claim 1, wherein the fan speed may be modulated continuously or intermittently during the analysis stage or during a cooling stage.

16. The gas chromatography system of claim 1, wherein the controller is configured to linearly link the fan speed to the degree of opening of at least one of the air intake aperture and the air exhaust aperture.

17. The gas chromatography system of claim 1, wherein the controller is configured to provide a temperature ramp during the analysis stage.

18. The gas chromatography system of claim 1, wherein the controller is configured to close at least one of the air intake aperture and the air exhaust aperture during the analysis stage, and further configured to open at least one of the air intake aperture and the air exhaust aperture during a cooling stage.

19. The gas chromatography system of claim 1, wherein, the air intake aperture and the air exhaust aperture may be controlled independently.

* * * * *

UNITED STATES PATENT AND TRADEMARK OFFICE
CERTIFICATE OF CORRECTION

| | | |
|---|---|---|
| PATENT NO. | : 8,104,326 B2 | Page 1 of 1 |
| APPLICATION NO. | : 11/841054 | |
| DATED | : January 31, 2012 | |
| INVENTOR(S) | : Andrew Tipler et al. | |

It is certified that error appears in the above-identified patent and that said Letters Patent is hereby corrected as shown below:

Title page, Item (75) Inventors: please replace inventor "Guiseppe Coppola" with inventor "Giuseppe Coppola."

Signed and Sealed this
Tenth Day of July, 2012

David J. Kappos
*Director of the United States Patent and Trademark Office*